US011492586B2

(12) United States Patent
Kanda

(10) Patent No.: US 11,492,586 B2
(45) Date of Patent: Nov. 8, 2022

(54) PARTICLE SORTING APPARATUS AND PARTICLE SORTING METHOD

(71) Applicant: Allied Flow Inc., Nishinomiya (JP)

(72) Inventor: Masahiko Kanda, Nishinomiya (JP)

(73) Assignee: Allied Flow Inc., Nishinomiya (JP)

( * ) Notice: Subject to any disclaimer, the term of this patent is extended or adjusted under 35 U.S.C. 154(b) by 282 days.

(21) Appl. No.: 16/717,431

(22) Filed: Dec. 17, 2019

(65) Prior Publication Data

US 2021/0039111 A1 Feb. 11, 2021

(30) Foreign Application Priority Data

Aug. 5, 2019 (JP) .............................. JP2019-143443

(51) Int. Cl.
*C12M 1/00* (2006.01)
*G01N 15/14* (2006.01)
*B03C 3/38* (2006.01)

(52) U.S. Cl.
CPC .............. *C12M 47/04* (2013.01); *B03C 3/38* (2013.01); *G01N 15/1456* (2013.01); *G01N 2015/149* (2013.01)

(58) Field of Classification Search
CPC ......... G01N 15/1456; G01N 2015/149; C12M 47/04; B03C 3/38
USPC ...................................................... 209/552
See application file for complete search history.

(56) References Cited

U.S. PATENT DOCUMENTS

| 5,700,692 | A | 12/1997 | Sweet |
| 6,372,506 | B1 | 4/2002 | Norton |
| 10,386,287 | B2 * | 8/2019 | Otsuka ............... G01N 15/1404 |
| 2013/0337575 | A1 | 12/2013 | Fox et al. |
| 2014/0193059 | A1 | 7/2014 | Muraki |
| 2015/0068957 | A1 * | 3/2015 | Otsuka ............... G01N 15/1425 |
| | | | 209/577 |
| 2015/0285727 | A1 | 10/2015 | Muraki |
| 2017/0010203 | A1 | 1/2017 | Otsuka et al. |
| 2018/0045638 | A1 | 2/2018 | Otsuka et al. |
| 2018/0058999 | A1 | 3/2018 | Otsuka et al. |
| 2019/0143330 | A1 | 5/2019 | Kanda |
| 2019/0219494 | A1 | 7/2019 | Otsuka et al. |

FOREIGN PATENT DOCUMENTS

| CN | 1950690 A | * | 4/2007 | ......... G01N 15/1459 |
| CN | 103364325 A | * | 10/2013 | ............ G01N 15/14 |
| CN | 103718020 A | * | 4/2014 | ............. B03C 7/003 |
| CN | 103364325 B | * | 9/2017 | ............ G01N 15/14 |
| JP | 2006-504970 A | | 2/2006 | |
| JP | 4304195 B2 | | 7/2009 | |
| JP | 2014-512549 A | | 5/2014 | |
| JP | 2015-152439 A | | 8/2015 | |
| JP | 2016-530519 A | | 9/2016 | |

(Continued)

*Primary Examiner* — Terrell H Matthews
(74) *Attorney, Agent, or Firm* — Sughrue Mion, PLLC

(57) ABSTRACT

A first imaging unit obtains an image of at least one of a jet flow, droplets or satellite drops. Based on a feature value of the at least one of the jet flow, the droplets or the satellite drops in the image, a controller controls a timing of starting to supply charges from a charge supply unit to a final jet flow droplet in one period of vibrations of a vibration element or an amplitude of a drive voltage applied to the vibration element so as to cause variation of a side stream to fall within a reference range.

11 Claims, 12 Drawing Sheets

(56) References Cited

FOREIGN PATENT DOCUMENTS

| | | | | |
|---|---|---|---|---|
| JP | 2017122734 A | * | 7/2017 | ............ B01L 3/0268 |
| JP | 2017-201278 A | | 11/2017 | |
| JP | 2020510222 A | * | 4/2018 | ......... G01N 15/1425 |
| WO | 2004/042647 A1 | | 5/2004 | |
| WO | 2012/148584 A1 | | 11/2012 | |
| WO | 2013/145905 A1 | | 10/2013 | |
| WO | 2014/115409 A1 | | 7/2014 | |
| WO | 2015/023916 A1 | | 2/2015 | |
| WO | WO-2016035284 A1 | * | 3/2016 | ........ B01L 3/502784 |

\* cited by examiner

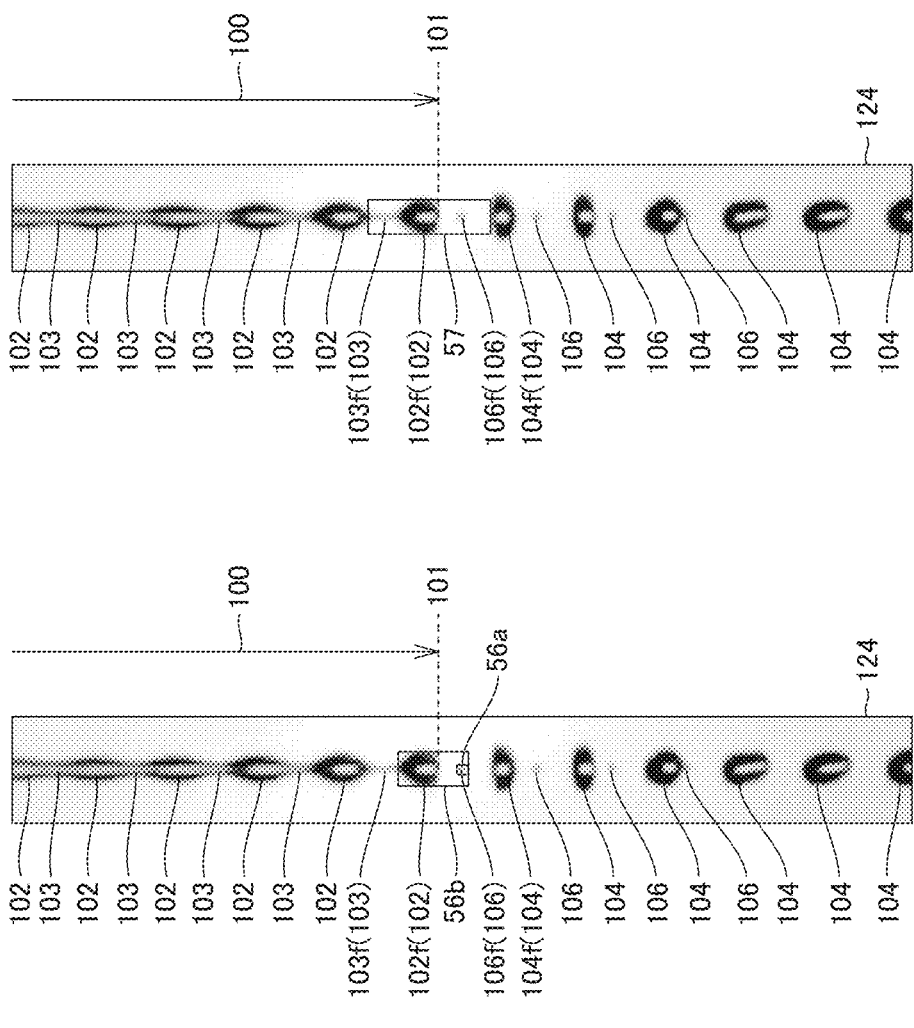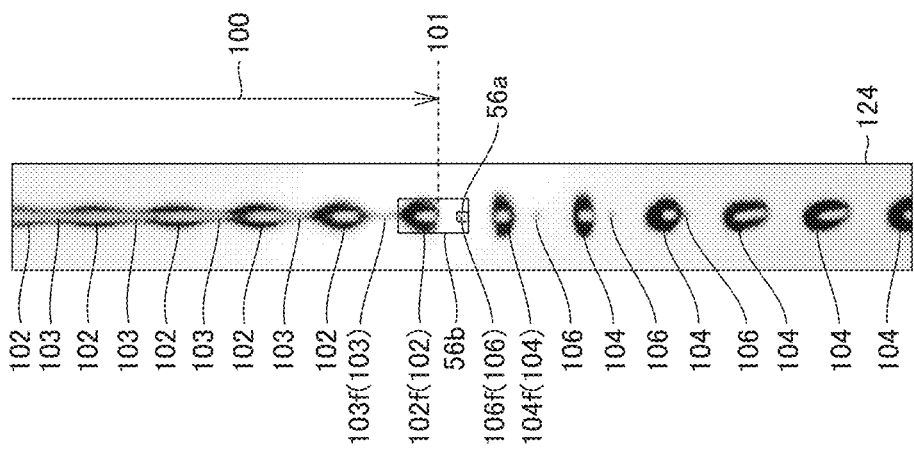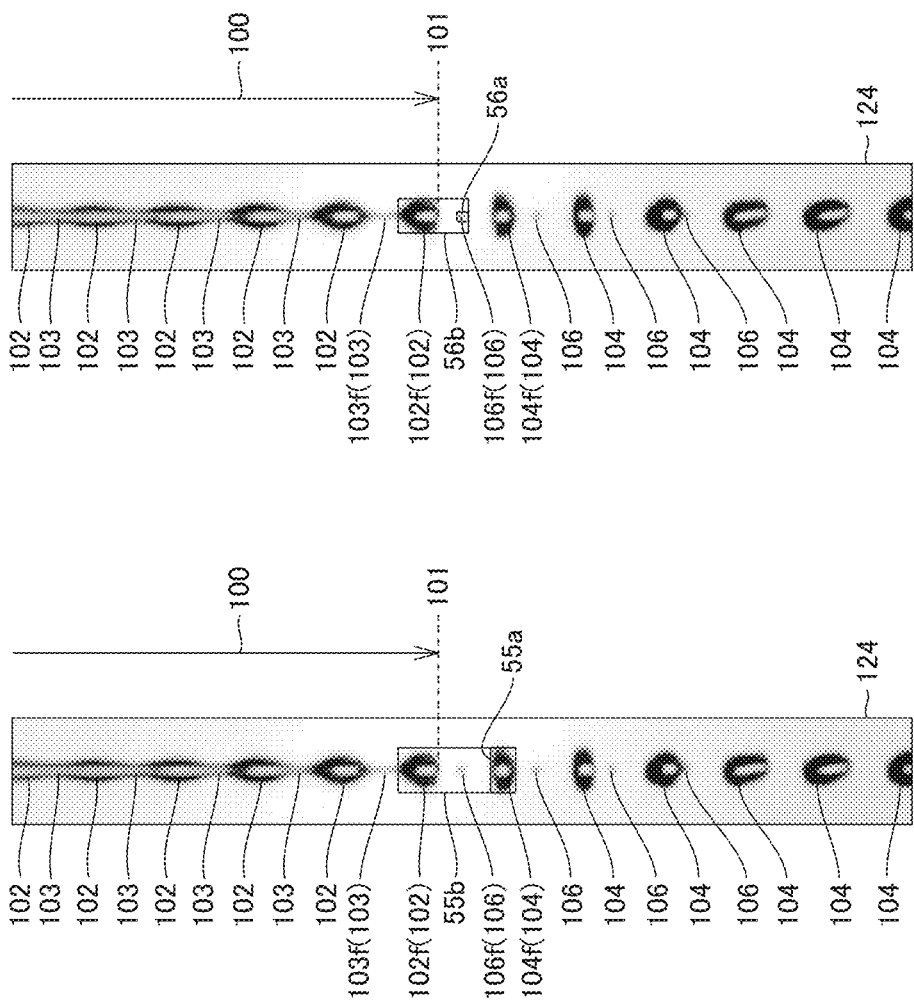

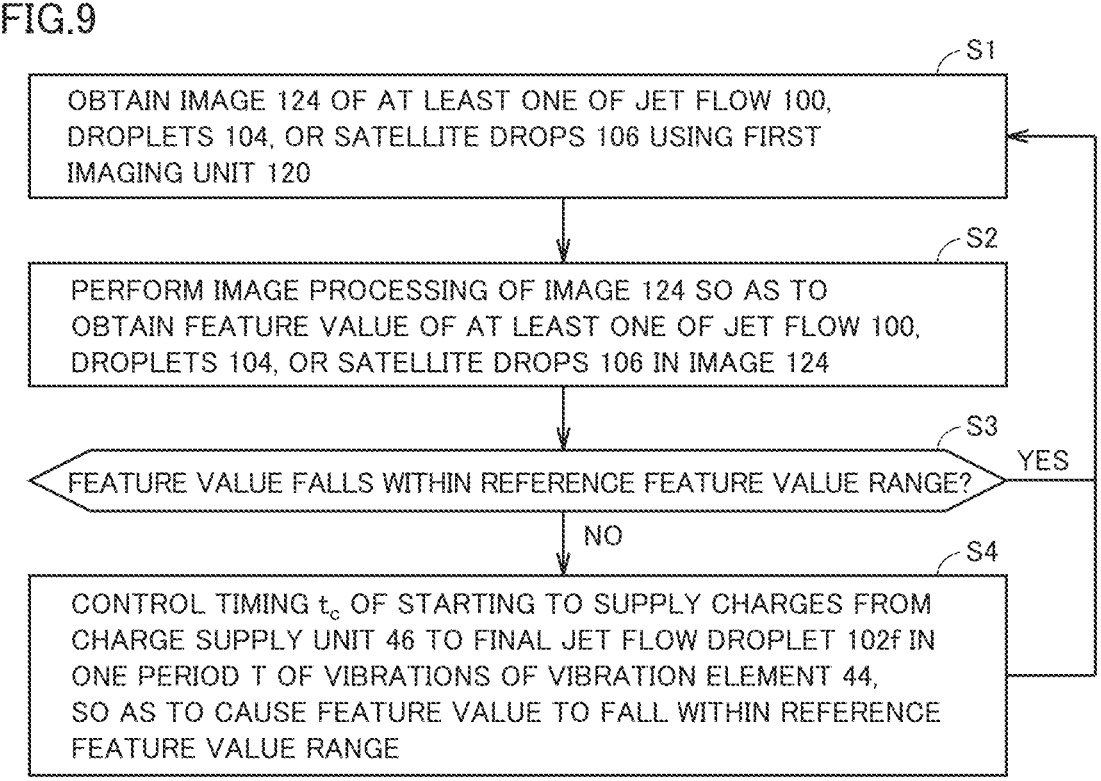

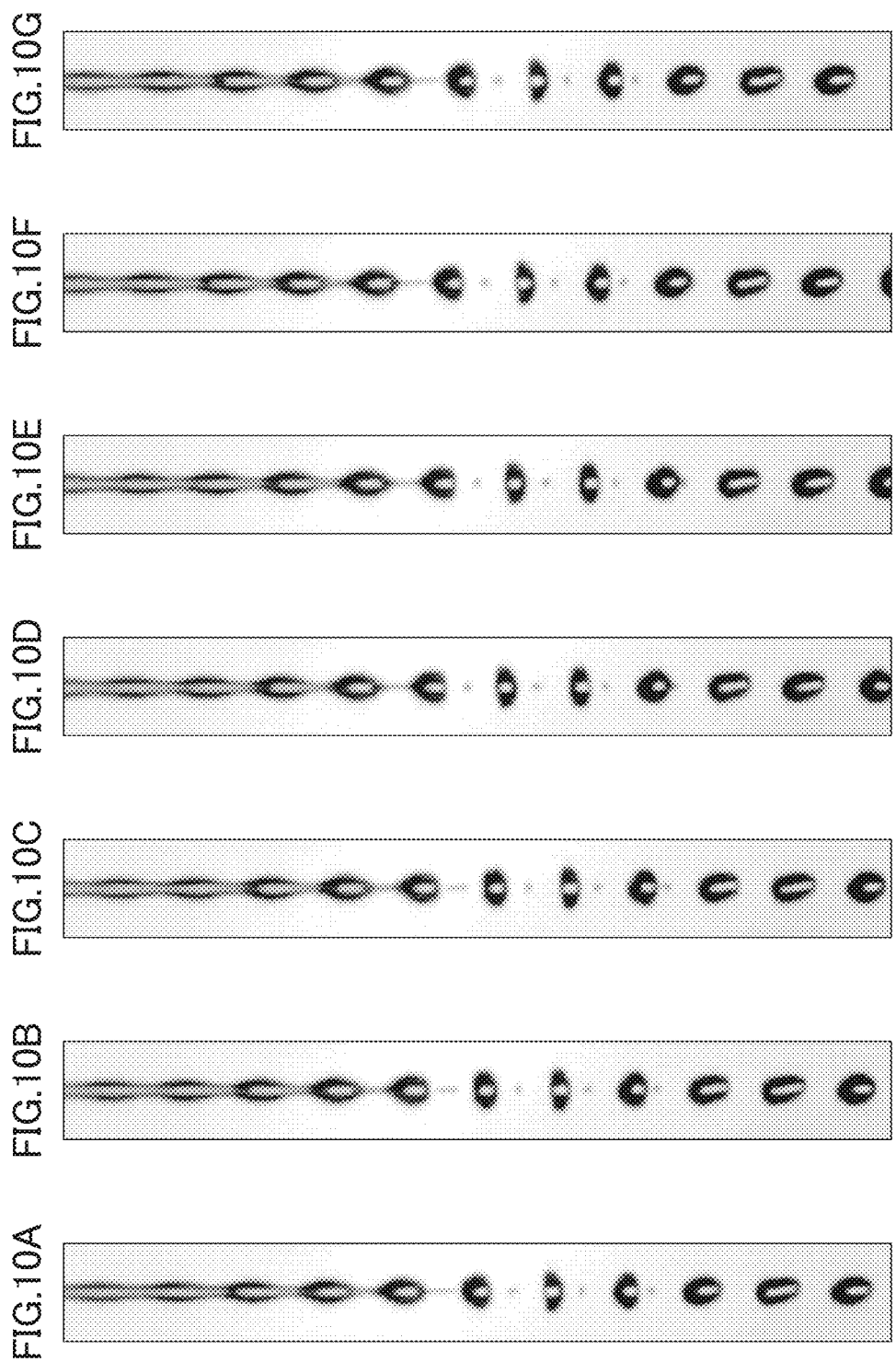

PARTICLE SORTING APPARATUS AND PARTICLE SORTING METHOD

BACKGROUND OF THE INVENTION

Field of the Invention

The present disclosure relates to a particle sorting apparatus and a particle sorting method.

Description of the Background Art

Due to progress in biotechnology, in various fields including medical science and biology, a demand has been increased for an apparatus that performs a process such as sorting or analysis on a multiplicity of cell particles, which are exemplary particles. As one example of such an apparatus, Japanese Patent Laying-Open No. 2017-201278 discloses a cell sorter.

SUMMARY OF THE INVENTION

An object of the present disclosure is to provide a particle sorting apparatus and a particle sorting method, by each of which particles can be sorted more stably with higher precision.

A particle sorting apparatus according to one aspect of the present disclosure includes a flow cell, a vibration element, a charge supply unit, an imaging unit, a sorting unit, and a controller. The vibration element applies vibrations to a jet flow ejected from the flow cell. The charge supply unit supplies charges to a final jet flow droplet, the final jet flow droplet being closest to a break-off point of jet flow droplets included in the jet flow. The imaging unit obtains an image of at least one of the jet flow, droplets or satellite drops, the droplets and the satellite drops being broken off from the jet flow. The sorting unit deflects the droplets. The controller controls, based on a feature value of the at least one of the jet flow, the droplets or the satellite drops in the image, a timing of starting to supply the charges from the charge supply unit to the final jet flow droplet in one period of the vibrations of the vibration element or an amplitude of a drive voltage applied to the vibration element so as to cause variation of a side stream to fall within a reference range, the side stream being formed by the droplets deflected by the sorting unit.

A particle sorting method according to one aspect of the present disclosure includes: applying vibrations from a vibration element to a jet flow ejected from a flow cell; supplying charges from a charge supply unit to a final jet flow droplet, the final jet flow droplet being closest to a break-off point of jet flow droplets included in the jet flow; obtaining, using an imaging unit, an image of at least one of the jet flow, droplets or satellite drops, the droplets and the satellite drops being broken off from the jet flow; and deflecting the droplets using a sorting unit. The particle sorting method according to one aspect of the present disclosure further includes controlling, based on a feature value of the at least one of the jet flow, the droplets or the satellite drops in the image, a timing of starting to supply the charges from the charge supply unit to the final jet flow droplet in one period of the vibrations of the vibration element or an amplitude of a drive voltage applied to the vibration element so as to cause variation of a side stream to fall within a reference range, the side stream being formed by the droplets deflected by the sorting unit.

The foregoing and other objects, features, aspects and advantages of the present disclosure will become more apparent from the following detailed description of the present disclosure when taken in conjunction with the accompanying drawings.

BRIEF DESCRIPTION OF THE DRAWINGS

Each of FIG. 6A

Each of FIG. 7A

Each of FIG. 8A to FIG. 8C shows an exemplary image obtained by the first imaging unit.

FIG. 9 shows a flowchart of control of a timing of starting to supply charges from a charge supply unit to a final jet flow droplet in one period T of vibrations of a vibration element, the control being performed in the particle sorting method according to the first embodiment.

Each of FIG. 10A to FIG. 10G shows an exemplary image obtained by the first imaging unit at the timing of starting to supply charges from the charge supply unit to the final jet flow droplet in one period of vibrations of the vibration element or when an amplitude of a drive voltage applied to the vibration element is gradually changed.

Figure 11:
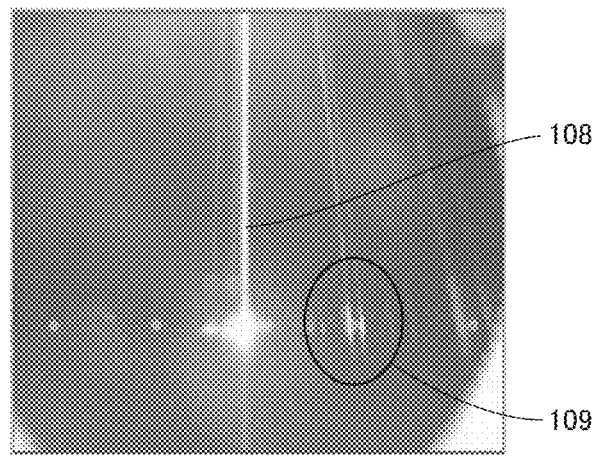

FIG. 11 shows an exemplary image of a side stream obtained by a second imaging unit.

Figure 12:
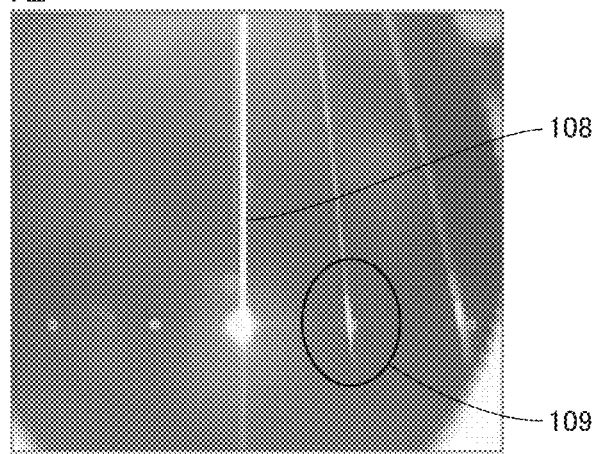

FIG. 12 shows an exemplary image of the side stream obtained by the second imaging unit.

Figure 13:
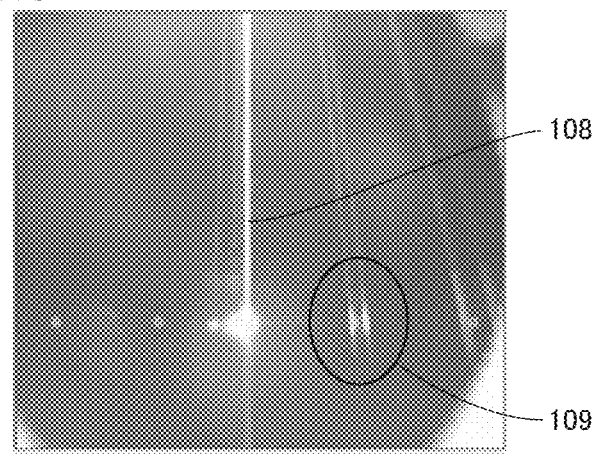

FIG. 13 shows an exemplary image of the side stream obtained by the second imaging unit.

Figure 14:
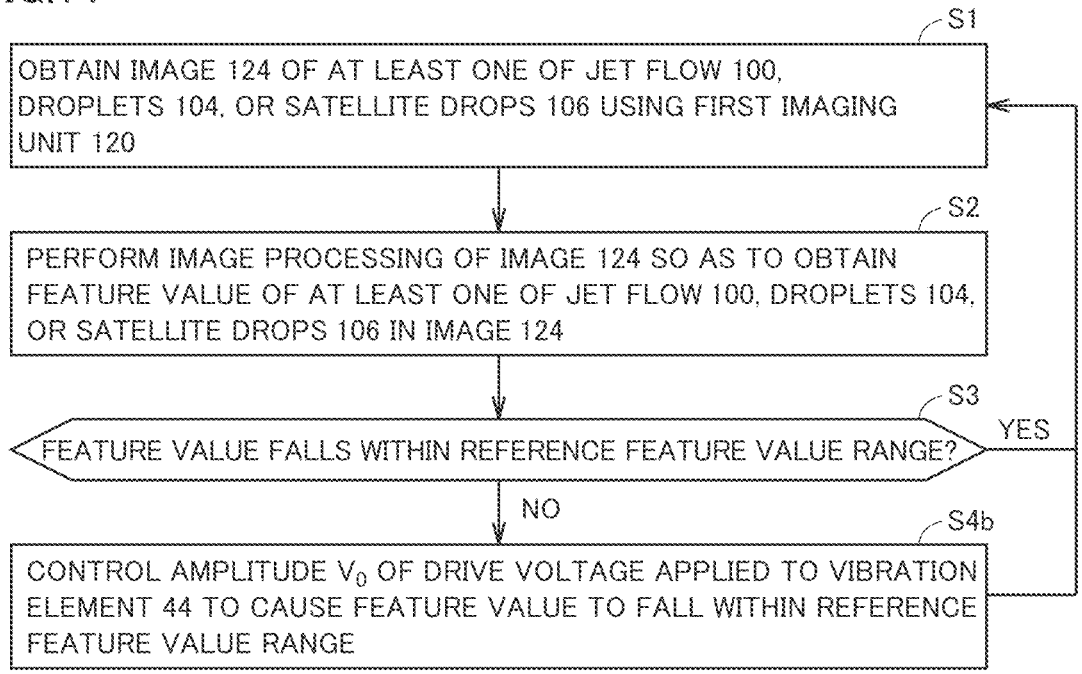

FIG. 14 is a schematic view showing a flowchart of control of the amplitude of the drive voltage applied to the vibration element, the control being performed in the particle sorting method according to the second embodiment.

Figure 15:
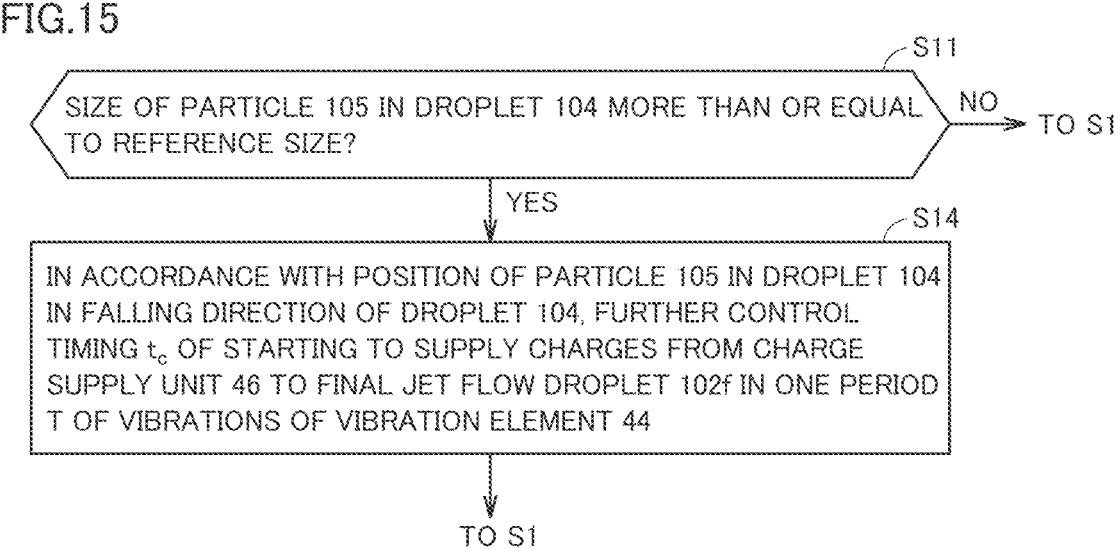

FIG. 15 shows a flowchart of another control of the timing of starting to supply charges from the charge supply unit to the final jet flow droplet in one period T of vibrations of the vibration element, the another control being performed in the particle sorting method according to the third embodiment.

Figure 16:
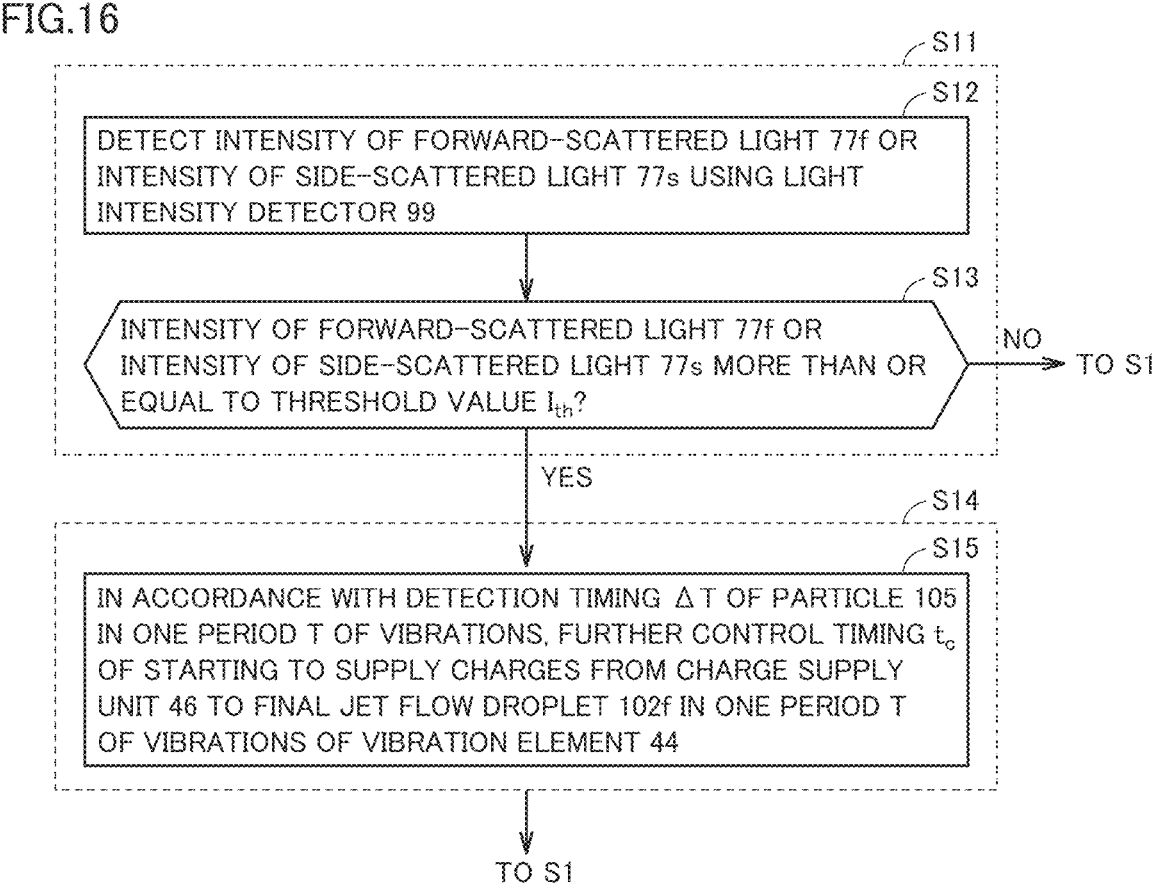

FIG. 16 shows a flowchart of one specific example of the another control of the timing of starting to supply charges from the charge supply unit to the final jet flow droplet in one period T of vibrations of the vibration element, the another control being performed in the particle sorting method according to the third embodiment.

Figure 17:
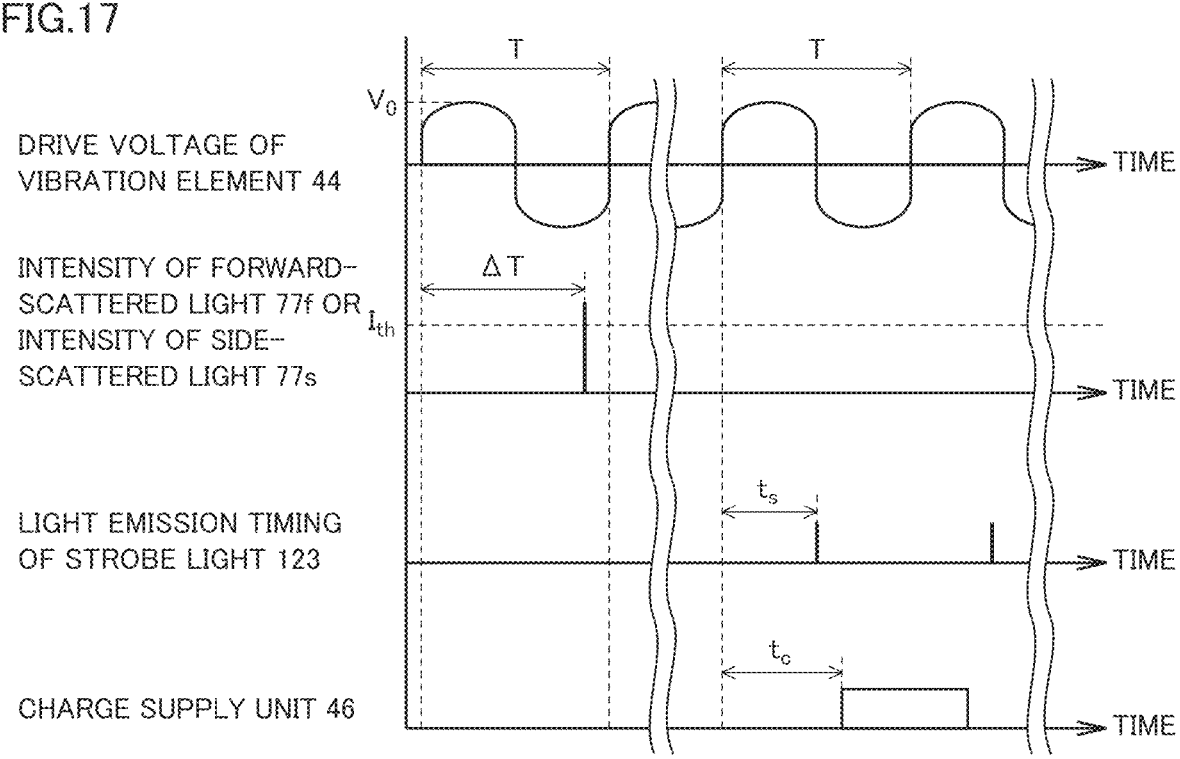

FIG. 17 shows a timing chart in the particle sorting method according to the third embodiment.

DESCRIPTION OF THE PREFERRED EMBODIMENTS

Hereinafter, embodiments of the present disclosure will be described. It should be noted that the same configurations are given the same reference numbers and will not be described repeatedly.

First Embodiment

With reference to FIG. 1 to FIG. 5, the following describes a particle sorting apparatus 1 according to a first embodiment. Particle sorting apparatus 1 mainly includes a flow chamber 10, a vibration element 44, a charge supply unit 46, a first light source unit 70, a detection optical system 83, a light intensity detector 99, a sorting unit 110, a collection unit 113, a first imaging unit 120, a strobe light 123, a controller 150, a storage unit 155, a base 5, and a wall 6. Particle sorting apparatus 1 further includes a vibration electrode 30, a second imaging unit 145, and a second light source unit 148.

Wall 6 is fixed to base 5. Flow chamber 10, sorting unit 110, and collection unit 113 are disposed at one side relative to wall 6. Vibration element 44, charge supply unit 46, detection optical system 83, light intensity detector 99, first imaging unit 120, second imaging unit 145, and controller 150 are disposed at the other side relative to wall 6.

Flow chamber 10 includes a chamber 11 and a flow cell 60.

A cavity 12 is provided inside chamber 11. A first conduit 21 connected to a first tank 20 is inserted in cavity 12 of chamber 11. When sorting particles 105 using particle sorting apparatus 1, a sample liquid including particles 105 is stored in first tank 20. Particles 105 are sample particles, such as biological particles (cells or chromosomes) labeled with fluorescent materials such as a fluorescent dye and a fluorescent antibody. In the case of aligning flow cell 60, each of particles 105 is a fluorescent bead (such as SPHERO™ Rainbow Calibration Particles RCP-30-5), for example. A second conduit 23 connected to a second tank 22 is inserted in cavity 12 of chamber 11. Second tank 22 stores a sheath liquid.

The sheath liquid stored in second tank 22 is supplied to cavity 12 of chamber 11 through second conduit 23. The liquid stored in first tank 20 and including particles 105 is supplied to cavity 12 of chamber 11 through first conduit 21. The liquid including particles 105 is supplied into cavity 12 of chamber 11 filled with the sheath liquid. In cavity 12 of chamber 11, the liquid including particles 105 is enclosed with the sheath liquid, thereby forming a sheath flow.

Flow cell 60 is attached to chamber 11. Flow cell 60 may be detachably coupled to chamber 11. Flow cell 60 includes a flow cell body portion 61. Flow cell body portion 61 is composed of a material (for example, a transparent inorganic material such as quartz, or a transparent resin material) transparent to laser light 71, fluorescence 77, side-scattered light 77s, and forward-scattered light 77f (see FIG. 2). Each of fluorescence 77 and side-scattered light 77s emitted from particle 105 irradiated with laser light 71.

A flow channel 65 is provided in flow cell body portion 61. A nozzle receiving portion 63 communicating with flow channel 65 is provided in flow cell body portion 61. Flow channel 65 communicates with cavity 12 of chamber 11. The sheath flow flows from cavity 12 to flow channel 65 of flow cell 60. In flow channel 65, particles 105 included in the sheath flow are arranged in one line along flow channel 65. Flow cell 60 includes a nozzle 68. A portion of nozzle 68 is received in nozzle receiving portion 63.

Figure 2:
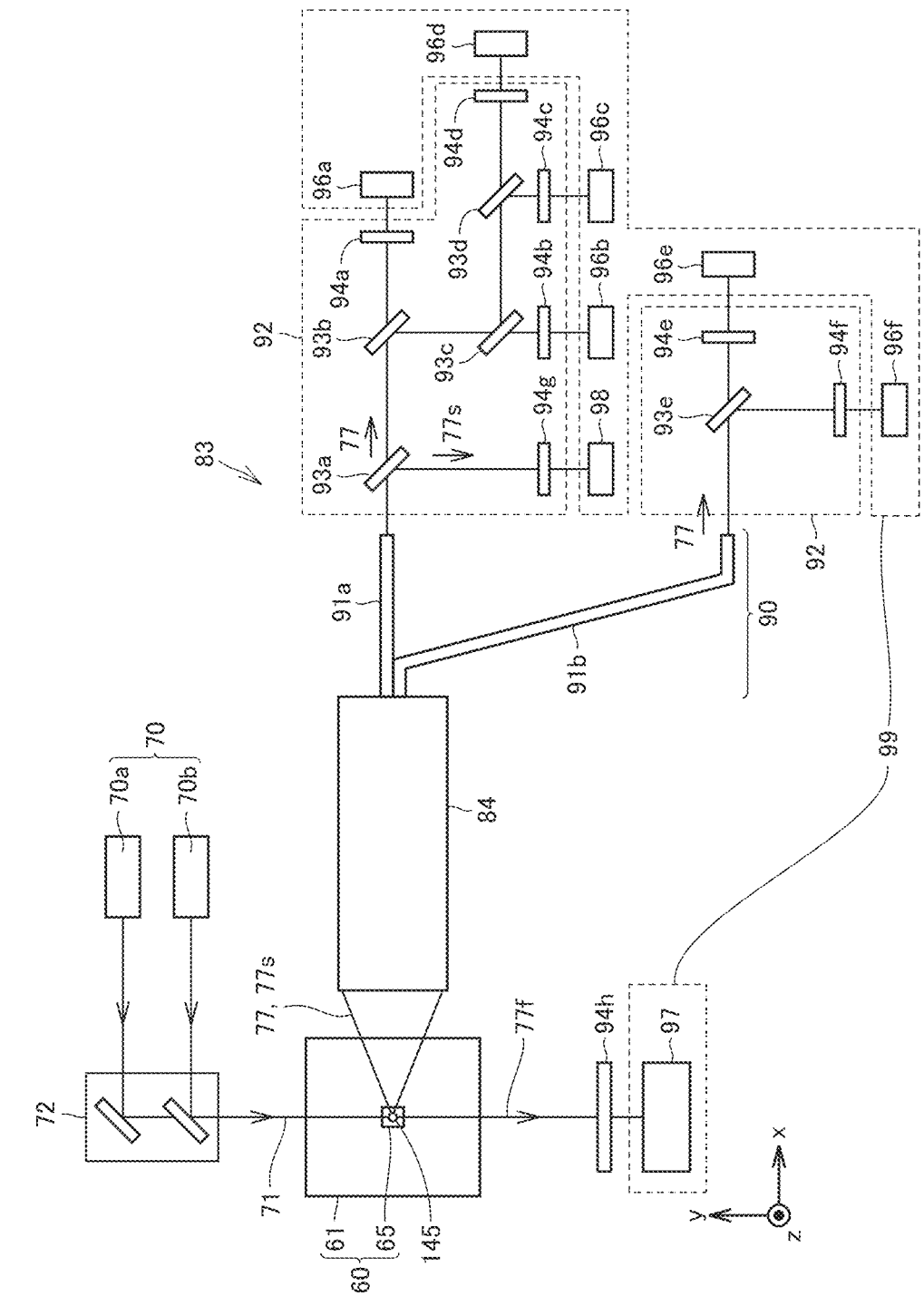
FIG. 2 is a schematic view showing an optical system included in the particle sorting apparatus according to each of the first embodiment to the third embodiment.

As shown in FIG. 2, each of particles 105 arranged in one line within flow channel 65 is irradiated with laser light 71 from first light source unit 70. Laser light 71 may include laser light having a plurality of wavelengths. Specifically, first light source unit 70 includes lasers 70a, 70b. The wavelength of the laser light emitted by laser 70a and the wavelength of the laser light emitted by laser 70b are different from each other. Each of particles 105 flowing in flow channel 65 is irradiated with laser light 71 emitted from first light source unit 70, via a light wavelength combining unit 72. Light wavelength combining unit 72 includes a dichroic mirror, for example. Fluorescence 77, forward-scattered light 77f, and side-scattered light 77s are emitted from particle 105. With laser light 71 including the light having the plurality of wavelengths, a plurality of pieces of identification information of each particle 105 can be obtained at one time. Particle 105 can be sorted efficiently.

Figure 1:
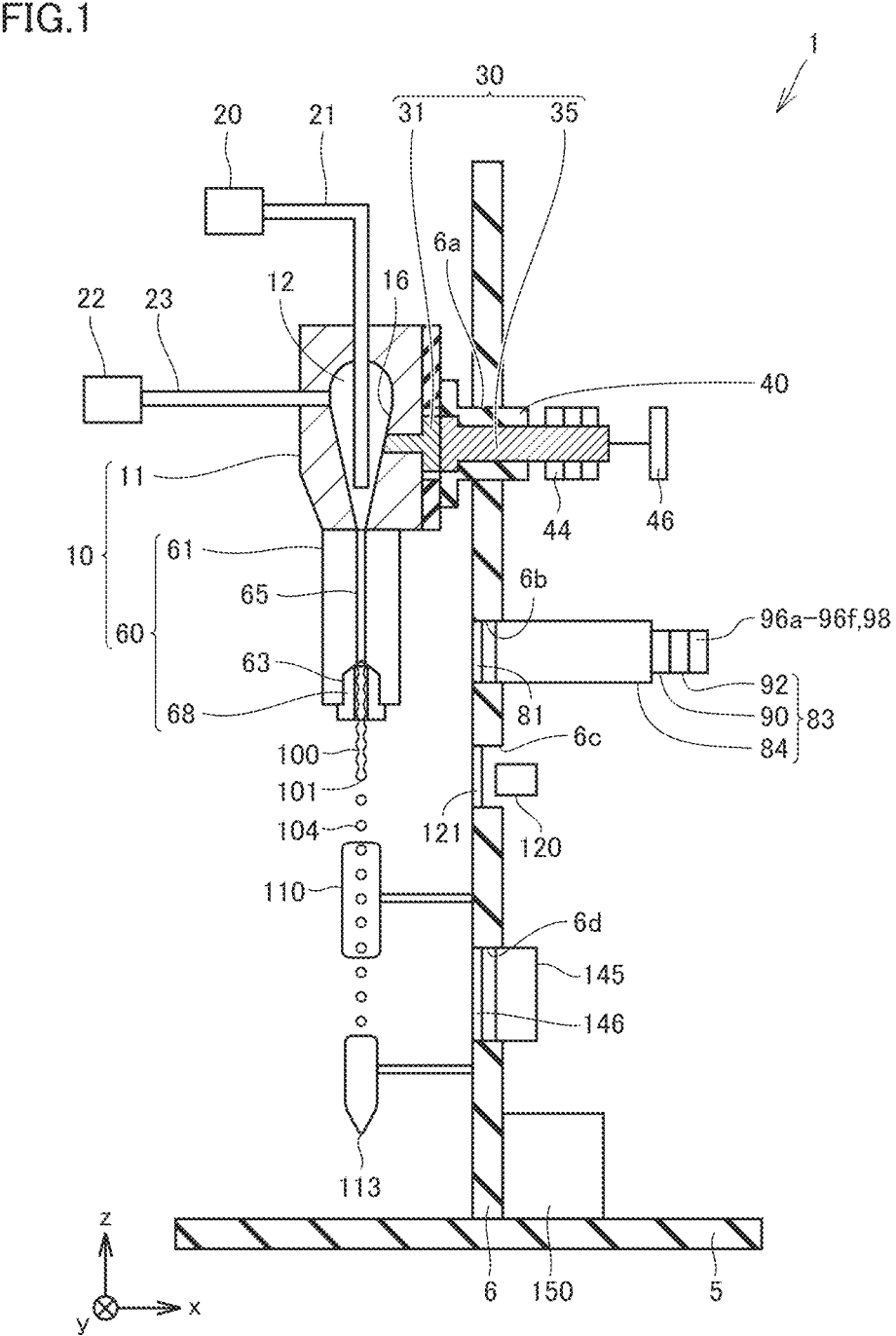
FIG. 1 is a schematic cross sectional view of a particle sorting apparatus according to each of a first embodiment to a third embodiment.

As shown in FIG. 1 and FIG. 2, detection optical system 83 faces flow cell 60 (a side surface of flow cell body portion 61) with a transparent window member 81 being interposed therebetween. Transparent window member 81 is fitted in an opening 6b of wall 6. Fluorescence 77 and side-scattered light 77s enter detection optical system 83 through transparent window member 81. Detection optical system 83 guides fluorescence 77 and side-scattered light 77s to light intensity detector 99.

As shown in FIG. 1 and FIG. 2, detection optical system 83 includes a detection side lens optical system 84, an optical fiber array 90, and a wavelength division unit 92. Detection side lens optical system 84 images fluorescence 77 and side-scattered light 77s on an incident surface of optical fiber array 90 with low chromatic aberration and low image aberration. Optical fiber array 90 is disposed between detection side lens optical system 84 and wavelength division unit 92. Optical fiber array 90 includes a plurality of optical fibers 91a, 91b. The plurality of optical fibers 91a, 91b are disposed to correspond to the plurality of lasers 70a, 70b, respectively. Optical fiber array 90 transmits fluorescence 77 and side-scattered light 77s to light intensity detector 99 (first light detectors 96a to 96f and a third light detector 98).

Wavelength division unit 92, which is disposed between optical fiber array 90 and light intensity detector 99 (specifically, first light detectors 96a to 96f and third light detector 98), divides fluorescence 77 and side-scattered light 77s. Wavelength division unit 92 includes dichroic mirrors 93a, 93b, 93c, 93d, 93e and wavelength filters 94a, 94b, 94c, 94d, 94e, 94f, 94g. Each of dichroic mirrors 93a to 93e reflects and permits passage of corresponding ones of beams of light in different wavelength regions. Each of wavelength filters 94a to 94f permits passage of a corresponding one of beams of light in different wavelength regions and blocks beams of light in the other wavelength regions. Wavelength filters 94a to 94f allow for improved detection precision for fluorescence 77 in first light detectors 96a to 96f. Wavelength filter 94g permits passage of side-scattered light 77s and blocks fluorescence 77. Wavelength filter 94g allows for improved detection precision for side-scattered light 77s in third light detector 98.

Light intensity detector 99 detects an intensity of light emitted from particle 105 included in the liquid flowing in flow channel 65. Specifically, light intensity detector 99 includes first light detectors 96a to 96f, second light detector 97, and third light detector 98. Each of first light detectors 96a to 96f measures an intensity of fluorescence 77 emitted from particle 105. Second light detector 97 measures an intensity of forward-scattered light 77f emitted from particle 105. Third light detector 98 measures an intensity of side-scattered light 77s emitted from particle 105. Each of first light detectors 96a to 96f, second light detector 97, and third light detector 98 is a photomultiplier tube (PMT) or a photodiode, for example. Identification information of particle 105 is obtained by controller 150 analyzing at least one of the intensity of fluorescence 77 detected by light intensity detector 99, the intensity of forward-scattered light 77f, or the intensity of side-scattered light 77s.

Wavelength filter 94h is disposed between flow cell 60 (flow cell body portion 61) and second light detector 97. Wavelength filter 94h permits passage of beams of light in a wavelength region including the wavelength of forward-scattered light 77f, and blocks beams of light in the other wavelength regions. Wavelength filter 94h allows for improved detection precision for forward-scattered light 77f in second light detector 97.

As shown in FIG. 1, vibration electrode 30 extends from cavity 12 of chamber 11 to outside of chamber 11. Vibration electrode 30 extends through opening 6a of wall 6 to pass through wall 6. Vibration electrode 30 includes a vibration electrode portion 31 and an electrically conductive portion 35. Vibration electrode portion 31 has a plurality of protrusions (not shown) fitted in a plurality of recesses (not shown) of electrically conductive portion 35, and is therefore electrically and mechanically connected to electrically conductive portion 35. Vibration electrode portion 31 is positioned relative to electrically conductive portion 35.

Vibration electrode portion 31 is provided in chamber 11. Vibration electrode portion 31 extends from cavity 12 of chamber 11 to the outside of chamber 11. An end surface 33 of vibration electrode portion 31 is exposed to cavity 12 of chamber 11. End surface 33 of vibration electrode portion 31 is smoothly continuous to a surface 16 defined by cavity 12 of chamber 11. The sheath flow in cavity 12 of chamber 11 can be prevented from being disturbed by end surface 33 of vibration electrode portion 31.

Electrically conductive portion 35 is inserted in opening 6a of wall 6, and is therefore attached to wall 6. Electrically conductive portion 35 extends through opening 6a to pass through wall 6. Specifically, electrically conductive portion 35 is received in an insulation sleeve 40. Insulation sleeve 40 is inserted in opening 6a.

Vibration electrode portion 31 is detachably connected to electrically conductive portion 35. Accordingly, flow chamber 10 can be attached to and detached from wall 6. Used flow chamber 10 can be readily exchanged with a flow chamber 10 sterilized by applying radiation or heat.

Vibration element 44 is connected to vibration electrode 30. Specifically, vibration element 44 is coupled to electrically conductive portion 35. Vibration element 44 has a ring shape, and electrically conductive portion 35 is fitted in the hole of vibration element 44. Vibrations (for example, ultrasonic vibrations) of vibration element 44 are transmitted to the sheath flow in cavity 12 of chamber 11 via vibration electrode 30. Vibration element 44 is a piezoelectric element, for example.

A jet flow 100 is sent out from nozzle 68. The vibrations generated in vibration element 44 are transmitted to jet flow 100. That is, vibration element 44 applies vibrations to jet flow 100 ejected from flow cell 60. Accordingly, jet flow 100 is broken off into a droplet 104 at break-off point 101, which is a lower end portion of jet flow 100. The number of droplets 104 generated per unit time is more than the number of particles 105 flowing in flow cell 60 per unit time. Particles 105 are included in parts of droplets 104. In this way, a stream 107 of droplets 104 is obtained.

Charge supply unit 46 is connected to electrically conductive portion 35. Charge supply unit 46 supplies charges corresponding to the identification information of particle 105, to a final jet flow droplet 102f via vibration electrode 30, the sheath flow, and jet flow 100. Among jet flow droplets 102 included in jet flow 100, final jet flow droplet 102f is closest to break-off point 101 of jet flow 100. Specifically, in accordance with the identification information of particle 105 included in final jet flow droplet 102f, charge supply unit 46 changes polarity and amount of charges to be supplied to final jet flow droplet 102f.

In the present specification, jet flow droplet 102 refers to a droplet 104 included in jet flow 100 yet to be broken off into droplet 104. Jet flow droplets 102 are connected to one another at constriction portions 103 of jet flow 100. Parts of jet flow droplets 102 include particles 105. Each of constriction portions 103 does not include a particle 105.

Figure 3:
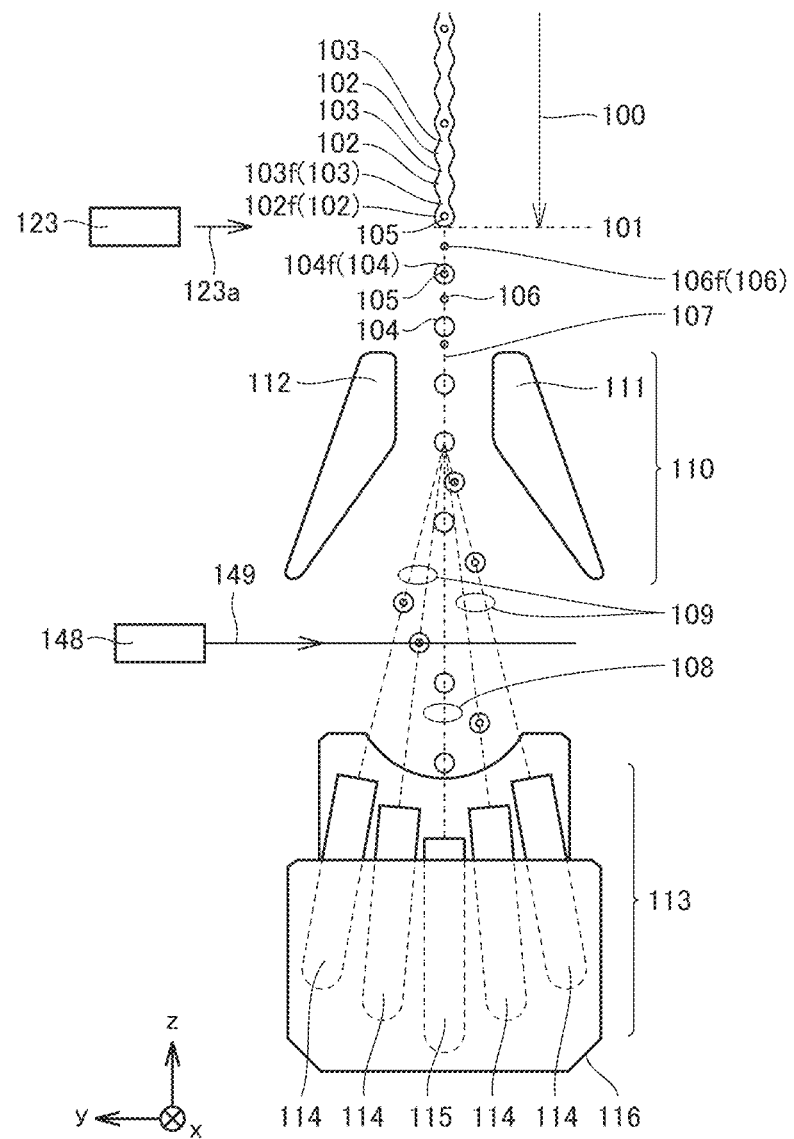
FIG. 3 is a schematic partial enlarged view of a sorting unit and a sample collection unit included in the particle sorting apparatus according to each of the first embodiment to the third embodiment.

As shown in FIG. 3, sorting unit 110 is a deflector that changes a falling direction of a droplet 104. Sorting unit 110 is attached to wall 6. Specifically, sorting unit 110 includes a pair of deflection electrodes 111, 112. By applying voltage between deflection electrodes 111, 112, an electric field is formed between deflection electrodes 111, 112. Each droplet 104 supplied with the charges from charge supply unit 46 receives force by the electric field between deflection electrodes 111, 112. Depending on the polarity and amount of charges supplied to droplet 104, the falling direction of droplet 104 is changed. Stream 107 of droplets 104 is separated into: a center stream 108 formed by droplets 104 unchanged in the falling direction by sorting unit 110; and side streams 109 formed by droplets 104 changed in the falling direction by sorting unit 110.

Collection unit 113 includes a plurality of sample collection members 114 and a waste liquid collection member 115. Collection unit 113 further includes a holder 116 that holds the plurality of sample collection members 114 and waste liquid collection member 115. Holder 116 is attached to wall 6. Droplets 104 included in side streams 109 are caught in corresponding sample collection members 114. In this way, particles 105 included in droplets 104 can be sorted in accordance with respective pieces of identification information of particles 105. Droplets 104 included in center stream 108 are caught in waste liquid collection member 115.

Strobe light 123 illuminates at least one of jet flow 100, droplets 104, or satellite drops 106. Droplets 104 and satellite drops 106 are broken off from jet flow 100. Specifically, strobe light 123 illuminates jet flow 100, droplets 104, and satellite drops 106. Droplets 104 include particles 105. Each of satellite drops 106 has a size smaller than that of each droplet 104, and includes no particle 105.

Figure 5:
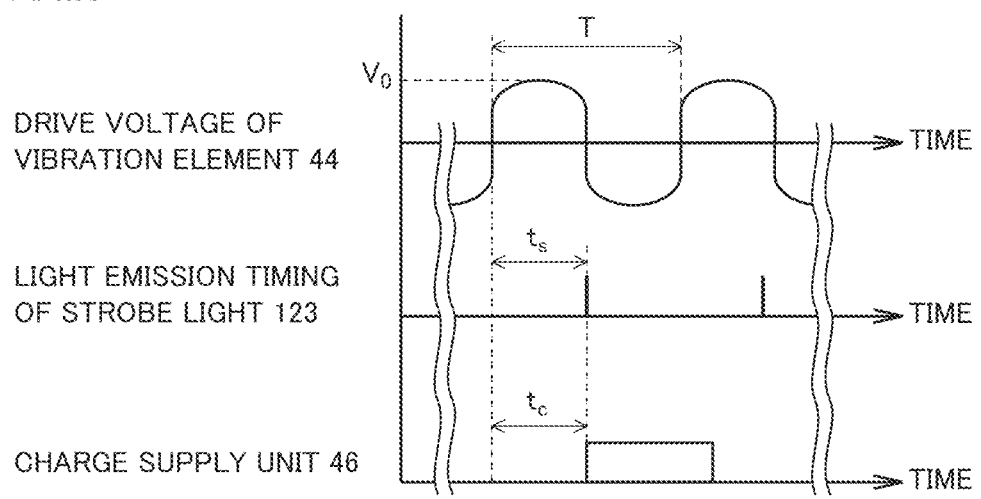
FIG. 5 shows a timing chart in a particle sorting method according to each of the first embodiment and the second embodiment.

As shown in FIG. 5, a light emission timing $t_s$ of strobe light 123 in one period T of vibrations of vibration element 44 is in synchronization with a timing $t_c$ of starting to supply charges from charge supply unit 46 to final jet flow droplet 102f in one period T of vibrations of vibration element 44. Accordingly, an image 124 of at least one of jet flow 100, droplets 104, or satellite drops 106 at timing $t_c$ can be obtained using first imaging unit 120. In the present embodiment, light emission timing $t_s$ of strobe light 123 is also changed in accordance with a change of timing $t_c$ of starting to supply charges from charge supply unit 46 to final jet flow droplet 102f in one period T of vibrations of vibration element 44. Strobe light 123 is an LED lamp, for example.

First imaging unit 120 faces transparent window member 121 fitted in opening 6c of wall 6. First imaging unit 120 obtains image 124 of at least one of jet flow 100, droplets 104, or satellite drops 106. Specifically, first imaging unit 120 obtains image 124 of jet flow 100, droplets 104, and satellite drops 106. Image 124 obtained by first imaging unit 120 may include an image of break-off point 101. First imaging unit 120 is not limited particularly and is a CCD camera or a CMOS camera, for example.

Second light source unit 148 emits second illumination light 149 toward side streams 109. Second light source unit 148 is a laser or a lamp, for example. When each of side streams 109 is irradiated with second illumination light 149, scattered light is generated in side stream 109.

Second imaging unit 145 faces a transparent window member 146 fitted in an opening 6d of wall 6. Second imaging unit 145 obtains an image of the scattered light from side stream 109. From the image obtained by second imaging unit 145, a degree of variation of each of side streams 109 can be found. Second imaging unit 145 is not limited particularly, and is a CCD camera or a CMOS camera, for example.

Figure 4:
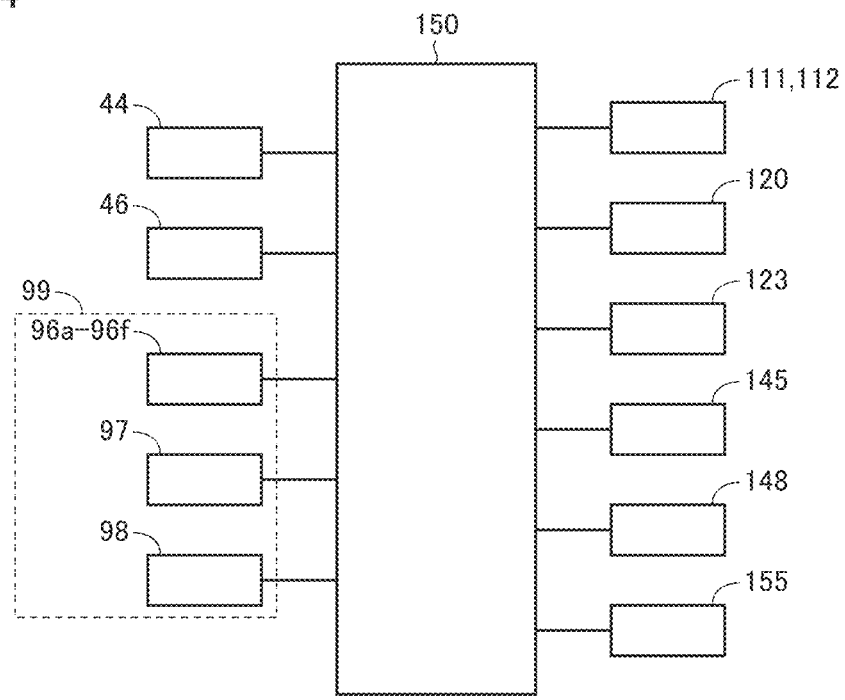
FIG. 4 is a control block diagram of the particle sorting apparatus according to each of the first embodiment to the third embodiment.

As shown in FIG. 4, controller 150 is communicatively connected to vibration element 44, charge supply unit 46, light intensity detector 99 (first light detectors 96a to 96f, second light detector 97, and third light detector 98), deflection electrodes 111, 112, first imaging unit 120, strobe light 123, second imaging unit 145, second light source unit 148, and storage unit 155.

Storage unit 155 is a hard disk or a semiconductor memory, for example. In storage unit 155, information is stored such as: the intensity of fluorescence 77 measured by each of first light detectors 96a to 96f; the intensity of forward-scattered light 77f measured by second light detector 97; the intensity of side-scattered light 77s measured by third light detector 98; image 124 obtained by first imaging unit 120; and the image obtained by second imaging unit 145, for example. Controller 150 sends these pieces of information to storage unit 155 and reads them from storage unit 155.

Controller 150 is a processor such as a CPU, for example. Controller 150 receives the intensity of fluorescence 77 measured by each of first light detectors 96a to 96f. Controller 150 receives the intensity of forward-scattered light 77f measured by second light detector 97. Controller 150 receives the intensity of side-scattered light 77s measured by third light detector 98. Controller 150 obtains the identification information of particle 105 by analyzing at least one of the intensity of fluorescence 77, the intensity of forward-scattered light 77f, or the intensity of side-scattered light 77s each detected by light intensity detector 99.

Controller 150 controls amplitude $V_0$, frequency, and the like of a drive voltage applied to vibration element 44. In this way, the amplitude, frequency, and the like of the vibrations (for example, ultrasonic vibrations) supplied from vibration element 44 to jet flow 100 are controlled. In the present embodiment, controller 150 controls amplitude $V_0$ of the drive voltage of vibration element 44 to be constant. Moreover, controller 150 controls the electric field applied between deflection electrodes 111, 112.

Controller 150 controls charge supply unit 46. Specifically, in accordance with the identification information of particle 105, controller 150 controls the polarity and amount of charges to be supplied from charge supply unit 46 to final jet flow droplet 102f. Moreover, controller 150 changes timing $t_c$ of starting to supply charges from charge supply unit 46 to final jet flow droplet 102f in one period T of vibrations of vibration element 44. By changing timing $t_c$, the state of jet flow 100, droplet 104, or satellite drop 106 at timing $t_c$ can be changed as shown in FIG. 10A to FIG. 10G, for example.

Controller 150 controls strobe light 123 to synchronize light emission timing $t_s$ of strobe light 123 in one period T of vibrations of vibration element 44, with timing $t_c$ of starting to supply charges from charge supply unit 46 to final jet flow droplet 102f in one period T of vibrations of vibration element 44. Accordingly, image 124 of at least one of jet flow 100, droplets 104, or satellite drops 106 at timing $t_c$ can be obtained using first imaging unit 120.

Controller 150 performs image processing of image 124 obtained by first imaging unit 120. For example, controller 150 performs image processing of image 124 of at least one of jet flow 100, droplets 104, or satellite drops 106 so as to calculate a feature value of at least one of jet flow 100, droplets 104, or satellite drops 106. Controller 150 performs image processing of the image obtained by second imaging unit 145.

Based on the feature value of at least one of jet flow 100, droplets 104, or satellite drops 106 included in image 124 obtained by first imaging unit 120, controller 150 controls timing $t_c$ of starting to supply charges from charge supply unit 46 to final jet flow droplet 102f in one period T of vibrations of vibration element 44, so as to cause variation of each side stream 109 to fall within a reference range, side stream 109 being formed by droplets 104 deflected by sorting unit 110. The variation of side stream 109 within the reference range corresponds to side stream 109 seen as one line in the image obtained by second imaging unit 145, for example. One period T of vibrations is a reciprocal of a frequency of vibrations applied from vibration element 44 to jet flow 100. The state of jet flow 100, droplets 104, or satellite drops 106 at timing $t_c$ of starting to supply charges from charge supply unit 46 to final jet flow droplet 102f in one period T of vibrations of vibration element 44 can be maintained to fall within an appropriate range, whereby the variation of side stream 109 can be reduced.

The following describes examples of the feature value obtained from image 124.

Figure 6A:
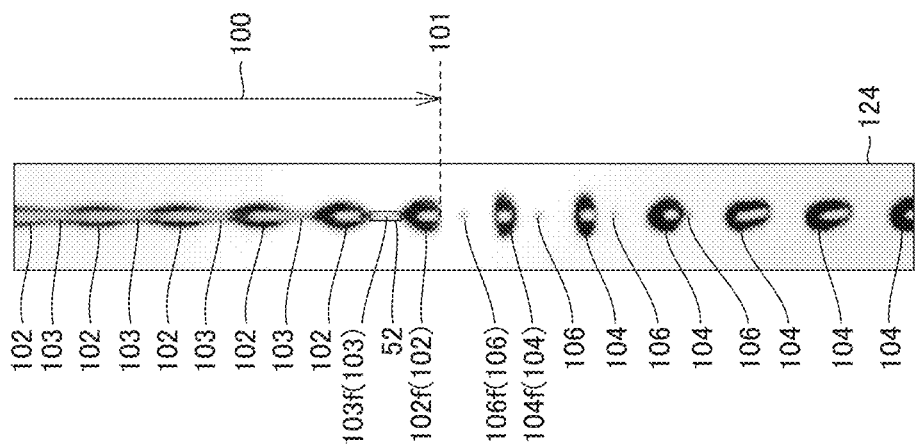
FIG. 6B shows an exemplary image obtained by a first imaging unit.

As shown in FIG. 6A, a first example of the feature value includes at least one of length, width, circumferential length, or area of final jet flow droplet 102f. The length of final jet flow droplet 102f refers to a length of final jet flow droplet 102f in a flow direction (z direction) of jet flow 100. The width of final jet flow droplet 102f refers to a length of final jet flow droplet 102f in a direction perpendicular to the flow direction (z direction) of jet flow 100.

The length, width, circumferential length, or area of final jet flow droplet 102f is calculated by performing image processing of a region of image 124 within a rectangular frame 51 that circumscribes final constriction portion 103f. Rectangular frame 51 can be defined by performing image processing of image 124. For example, the length of final jet flow droplet 102f is given by the length of rectangular frame 51 that circumscribes final jet flow droplet 102f. The width of final jet flow droplet 102f is given by the width of rectangular frame 51.

Figure 6B:
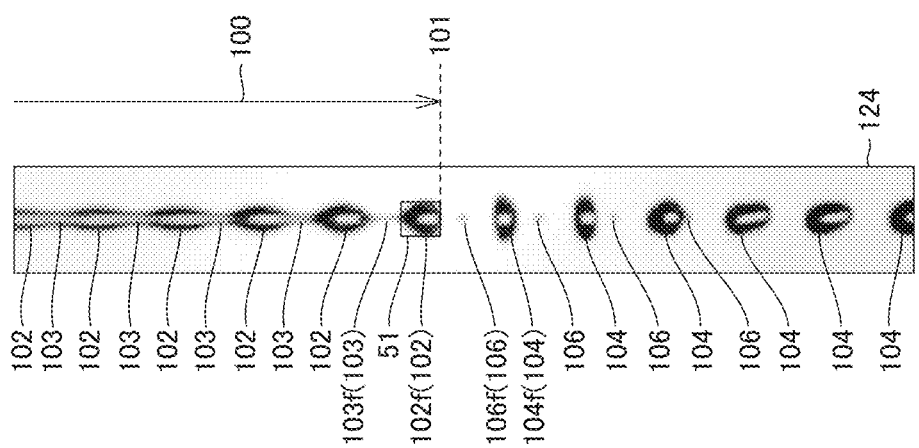

As shown in FIG. 6B, a second example of the feature value includes at least one of length, lower end width, circumferential length, or area of final constriction portion 103f of jet flow 100, final constriction portion 103f being connected to final jet flow droplet 102f. Final constriction portion 103f of constriction portions 103 included in jet flow 100 is closest to break-off point 101 of jet flow 100. The length of final constriction portion 103$f$ refers to a length of final constriction portion 103$f$ in the flow direction (z direction) of jet flow 100.

The length, lower end width, circumferential length, or area of final constriction portion 103$f$ is calculated by performing image processing of a region of image 124 within a rectangular frame 52 that circumscribes final constriction portion 103$f$. Rectangular frame 52 can be defined by performing image processing of image 124. The length of final constriction portion 103$f$ is given by the length of rectangular frame 52, for example. The lower end width of final constriction portion 103$f$ is given by the lower end width of rectangular frame 52.

Figure 7A:
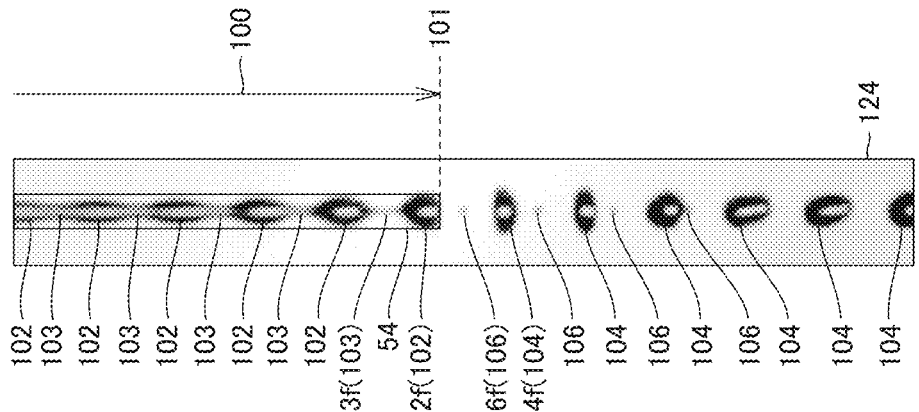
FIG. 7B shows an exemplary image obtained by the first imaging unit.

As shown in FIG. 7A, a third example of the feature value includes at least one of length, circumferential length, or area of final jet flow droplet 102$f$ and final constriction portion 103$f$. The length of final jet flow droplet 102$f$ and final constriction portion 103$f$ refers to a length of final jet flow droplet 102$f$ and final constriction portion 103$f$ in the flow direction (z direction) of jet flow 100.

The length, circumferential length, or area of final jet flow droplet 102$f$ and final constriction portion 103$f$ is calculated by performing image processing of a region of image 124 within a rectangular frame 53 that circumscribes final jet flow droplet 102$f$ and final constriction portion 103$f$. Rectangular frame 53 can be defined by performing image processing of image 124. The length of final jet flow droplet 102$f$ and final constriction portion 103$f$ is given by the length of rectangular frame 53, for example.

Figure 7B:
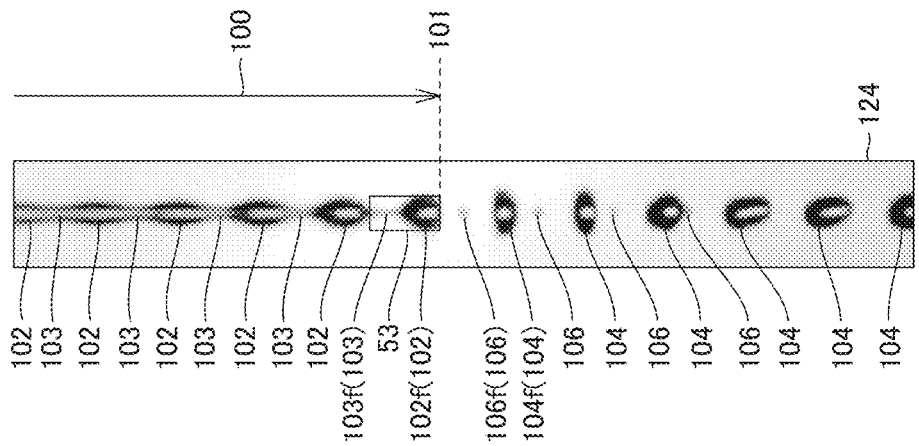

As shown in FIG. 7B, a fourth example of the feature value includes at least one of length, width, circumferential length, or area of jet flow 100 in image 124, or a position of the center of gravity of jet flow 100 in the flow direction (z direction) of jet flow 100 in image 124. The length of jet flow 100 refers to the length of jet flow 100 in the flow direction (z direction) of jet flow 100. The width of jet flow 100 refers to the length of jet flow 100 in the direction perpendicular to the flow direction (z direction) of jet flow 100.

The length, width, circumferential length, area, or position of the center of gravity of jet flow 100 in image 124 is calculated by performing image processing of a region of image 124 within a rectangular frame 54 that circumscribes jet flow 100. Rectangular frame 54 can be defined by performing image processing of image 124. The length of jet flow 100 is given by the length of rectangular frame 54, for example. The width of jet flow 100 is given by the width of rectangular frame 54. The position of the center of gravity of jet flow 100 is calculated through the following steps, for example. By performing binarization processing of image 124, a contour of jet flow 100 is specified. Based on the contour of jet flow 100, the position of the center of gravity of jet flow 100 is calculated.

As shown in FIG. 8A, a fifth example of the feature value includes at least one of length, width, circumferential length, or area of first droplet 104$f$, a position of center of gravity of first droplet 104$f$ in the flow direction (z direction) of the jet flow, or a distance between the lower end of final jet flow droplet 102$f$ and the upper end of first droplet 104$f$ (an interval between final jet flow droplet 102$f$ and first droplet 104$f$), first droplet 104$f$ being closest to final jet flow droplet 102$f$. Among droplets 104, first droplet 104$f$ is closest to final jet flow droplet 102$f$.

The length, width, circumferential length, or area of first droplet 104$f$, or the position of the center of gravity of first droplet 104$f$ in the flow direction (z direction) of the jet flow is calculated by performing image processing of a region of image 124 within a rectangular frame 55$a$ that circumscribes first droplet 104$f$. Rectangular frame 55$a$ can be defined by performing image processing of image 124. The length of first droplet 104$f$ is given by the length of rectangular frame 55$a$, for example. The width of first droplet 104$f$ is given by the width of rectangular frame 55$a$. The position of the center of gravity of first droplet 104$f$ is calculated through the following steps, for example. By performing binarization processing of image 124, a contour of first droplet 104$f$ is specified. Based on the contour of first droplet 104$f$, the position of the center of gravity of first droplet 104$f$ is calculated.

The distance between the lower end of final jet flow droplet 102$f$ and the upper end of first droplet 104$f$ (the interval between final jet flow droplet 102$f$ and first droplet 104$f$) is calculated by performing image processing of a region of image 124 in a rectangular frame 55$b$ including first droplet 104$f$ and final jet flow droplet 102$f$.

As shown in FIG. 8B, a sixth example of the feature value includes at least one of length, width, circumferential length, or area of first satellite drop 106$f$, a distance between the lower end of final jet flow droplet 102$f$ and the lower end of first satellite drop 106$f$, or a distance between the lower end of final jet flow droplet 102$f$ and the upper end of first satellite drop 106$f$ (an interval between final jet flow droplet 102$f$ and first satellite drop 106$f$). First satellite drop 106$f$ of satellite drops 106 is closest to break-off point 101.

The length, width, circumferential length, or area of first satellite drop 106$f$ is calculated by performing image processing of a region of image 124 in a rectangular frame 56$a$ that circumscribes first satellite drop 106$f$. Rectangular frame 56$a$ can be defined by performing image processing of image 124. The length of first satellite drop 106$f$ is given by the length of rectangular frame 56$a$, for example. The width of first satellite drop 106$f$ is given by the width of rectangular frame 56$a$.

The distance between the lower end of final jet flow droplet 102$f$ and the lower end of first satellite drop 106$f$ or the distance between the lower end of final jet flow droplet 102$f$ and the upper end of first satellite drop 106$f$ is calculated by performing image processing of a region in a rectangular frame 56$b$ including first satellite drop 106$f$ and final jet flow droplet 102$f$ in image 124.

As shown in FIG. 8C, a seventh example of the feature value includes at least one of area or circumferential length of final constriction portion 103$f$, final jet flow droplet 102$f$, and first satellite drop 106$f$ between the upper end of final constriction portion 103$f$ and the upper end of first droplet 104$f$, or a distance between the upper end of final constriction portion 103$f$ and the upper end of first droplet 104$f$.

The area or circumferential length of final constriction portion 103$f$, final jet flow droplet 102$f$, and first satellite drop 106$f$ between the upper end of final constriction portion 103$f$ and the upper end of first droplet 104$f$, or the distance between the upper end of final constriction portion 103$f$ and the upper end of first droplet 104$f$ is calculated by performing image processing of a region of image 124 within a rectangular frame 57. The upper end of rectangular frame 57 is in contact with the upper end of final constriction portion 103$f$. The lower end of rectangular frame 57 is in contact with the upper end of first droplet 104$f$.

An eighth example of the feature value is a combination of at least two of the first to seventh examples of the feature value. In order to maintain the state of jet flow 100, droplets 104, or satellite drops 106 to fall within an appropriate range at timing $t_c$ of starting to supply charges from charge supply unit 46 to final jet flow droplet 102$f$ in one period T of vibrations of vibration element 44, it is desirable to employ a combination of: the fourth example (FIG. 7B) of the feature value obtained by performing the image processing of the relatively large region; and any one of the first to third examples of the feature value and the fifth to seventh examples of the feature value, each of which is obtained by performing image processing of the relatively small region (FIG. 6A to FIG. 7A and FIG. 8A to FIG. 8C).

The following describes a particle sorting method according to the first embodiment.

In the particle sorting method according to the present embodiment, while sorting particle 105 based on the identification information of particle 105 obtained by light intensity detector 99 and controller 150, timing $t_c$ of starting to supply charges from charge supply unit 46 to final jet flow droplet 102f in one period T of vibrations of vibration element 44 is controlled, based on the feature value of at least one of jet flow 100, droplets 104, or satellite drops 106 in image 124 obtained using first imaging unit 120, so as to cause the variation of side stream 109 formed by droplets 104 deflected by sorting unit 110 to fall within the reference range. The state of jet flow 100, droplets 104, or satellite drops 106 at timing $t_c$ of starting to supply charges from charge supply unit 46 to final jet flow droplet 102f in one period T of vibrations of vibration element 44 can be maintained to fall within an appropriate range, whereby the variation of side stream 109 can be reduced.

Specifically, vibrations are applied from vibration element 44 to jet flow 100 ejected from flow cell 60. Charges are supplied from charge supply unit 46 to final jet flow droplet 102f. The polarity and amount of charges supplied from charge supply unit 46 to final jet flow droplet 102f are changed in accordance with the identification information of particle 105 included in final jet flow droplet 102f. Droplet 104 is deflected using sorting unit 110. In this way, particle 105 is sorted.

The following steps shown in FIG. 9 are performed while sorting particles 105. In the present embodiment, during the following steps, controller 150 controls amplitude $V_0$ of the drive voltage of vibration element 44 to be constant.

Image 124 of at least one of jet flow 100, droplets 104, or satellite drops 106 is obtained using first imaging unit 120 (S1). In one period T of vibrations of vibration element 44, controller 150 controls strobe light 123 to irradiate at least one of jet flow 100, droplets 104, or satellite drops 106 with first illumination light 123a at light emission timing $t_s$ that is in synchronization with timing $t_c$ of starting to supply charges from charge supply unit 46 to final jet flow droplet 102f. Accordingly, image 124 of at least one of jet flow 100, droplets 104, or satellite drops 106 at timing $t_c$ can be obtained using first imaging unit 120. Controller 150 stores image 124 into storage unit 155.

Then, timing $t_c$ of starting to supply charges from charge supply unit 46 to final jet flow droplet 102f in one period T of vibrations of vibration element 44 is controlled, based on the feature value of at least one of jet flow 100, droplets 104, or satellite drops 106 in image 124 obtained using first imaging unit 120, so as to cause the variation of side stream 109 formed by droplets 104 deflected by sorting unit 110 to fall within the reference range.

Specifically, controller 150 performs image processing of image 124 stored in storage unit 155, so as to obtain the feature value of at least one of jet flow 100, droplets 104, or satellite drops 106 in image 124 (S2). Controller 150 stores the feature value into storage unit 155.

Controller 150 reads the feature value and a reference feature value from storage unit 155, and determines whether or not the feature value falls within a reference feature value range (S3). The reference feature value range of at least one of jet flow 100, droplets 104, or satellite drops 106 is an exemplary reference range of the variation of side stream 109. When the feature value falls within the reference feature value range, the process returns to step S1.

When the feature value does not fall within the reference feature value range, controller 150 controls timing $t_c$ of starting to supply charges from charge supply unit 46 to final jet flow droplet 102f in one period T of vibrations of vibration element 44, so as to cause the feature value to fall within the reference feature value range (S4). In this way, timing $t_c$ is controlled to cause the variation of side stream 109 to fall within the reference range. Light emission timing $t_s$ of strobe light 123 in one period T of vibrations of vibration element 44 is also controlled in accordance with the change of timing $t_c$. When the feature value falls within the the reference feature value range as a result of controlling timing $t_c$, the process returns to step S1.

The reference range of the variation of side stream 109 is obtained before sorting particles 105, and is stored into storage unit 155. The following describes a method for obtaining the reference feature value range of at least one of jet flow 100, droplets 104, or satellite drops 106, which is one example of the reference range of the variation of side stream 109.

While obtaining the reference feature value range, a sheath liquid including no particle 105 is introduced into flow cell 60. Controller 150 supplies charges from charge supply unit 46 to final jet flow droplet 102f irrespective of an output from light intensity detector 99, thus obtaining side streams 109.

While changing timing $t_c$ of starting to supply charges from charge supply unit 46 to final jet flow droplet 102f in one period T of vibrations of vibration element 44, image 124 of at least one of jet flow 100, droplets 104, or satellite drops 106 at timing $t_c$ is obtained using first imaging unit 120. In order to obtain image 124 of at least one of jet flow 100, droplets 104, or satellite drops 106 at timing $t_c$, at least one of jet flow 100, droplets 104, or satellite drops 106 is irradiated with first illumination light 123a emitted from strobe light 123 at light emission timing $t_s$ that is in synchronization with timing $t_c$. When timing $t_c$ is changed, image 124 obtained by first imaging unit 120 is changed as shown in FIG. 10A to FIG. 10G, for example.

Furthermore, while changing timing $t_c$, side stream 109 is irradiated with second illumination light 149. When side stream 109 is irradiated with second illumination light 149, scattered light is generated in side stream 109. An image of the scattered light from side stream 109 is obtained using second imaging unit 145. When timing $t_c$ is changed, the image obtained by second imaging unit 145 is changed as shown in FIG. 11 to FIG. 13, for example.

When image 124 obtained by first imaging unit 120 is as shown in FIG. 10A to FIG. 10D, each of side streams 109 is divided into a plurality of partial side streams as shown in FIG. 11. Variation of each side stream 109 exceeds the reference range. When image 124 obtained by first imaging unit 120 is as shown in FIG. 10E and FIG. 10F, each of side streams 109 is seen as one line as shown in FIG. 12. Variation of each side stream 109 is in the reference range. When image 124 obtained by first imaging unit 120 is as shown in FIG. 10G, each of side streams 109 is divided into a plurality of partial side streams as shown in FIG. 13. Variation of each side stream 109 exceeds the reference range. Controller 150 stores image 124 shown in each of FIG. 10E and FIG. 10F as a reference image into storage unit 155.

Controller 150 performs image processing of each of the reference images stored in storage unit 155 so as to calculate a reference feature value of at least one of jet flow 100, droplets 104, or satellite drops 106. An example of the reference feature value obtained from the reference image is the same as the example of the feature value obtained from image 124 obtained by first imaging unit 120. Controller 150 calculates a reference feature value range based on the reference feature value obtained from each of the reference images. Controller 150 stores the reference feature value range into storage unit 155.

The following describes effects of particle sorting apparatus 1 and the particle sorting method according to the present embodiment.

A particle sorting apparatus 1 according to the present embodiment includes a flow cell 60, a vibration element 44, a charge supply unit 46, an imaging unit (first imaging unit 120), a sorting unit 110, and a controller 150. Vibration element 44 applies vibrations to a jet flow 100 ejected from flow cell 60. Charge supply unit 46 supplies charges to a final jet flow droplet 102$f$, final jet flow droplet 102$f$ being closest to a break-off point 101 of jet flow droplets 102 included in jet flow 100. The imaging unit (first imaging unit 120) obtains an image 124 of at least one of jet flow 100, droplets 104, or satellite drops 106, droplets 104 and satellite drops 106 being broken off from jet flow 100. Sorting unit 110 deflects droplets 104. Controller 150 controls, based on a feature value of the at least one of jet flow 100, droplets 104, or satellite drops 106 in image 124, a timing $t_c$ of starting to supply the charges from charge supply unit 46 to final jet flow droplet 102$f$ in one period T of the vibrations of vibration element 44 so as to cause variation of a side stream 109 to fall within a reference range, side stream 109 being formed by droplets 104 deflected by sorting unit 110.

A particle sorting method according to the present embodiment includes: applying vibrations from a vibration element 44 to a jet flow 100 ejected from a flow cell 60; supplying charges from a charge supply unit 46 to a final jet flow droplet 102$f$, final jet flow droplet 102$f$ being closest to a break-off point 101 of jet flow droplets 102 included in jet flow 100; obtaining, using an imaging unit (first imaging unit 120), an image 124 of at least one of jet flow 100, droplets 104, or satellite drops 106, droplets 104 and satellite drops 106 being broken off from jet flow 100; and deflecting droplets 104 using a sorting unit 110. The particle sorting method according to the present embodiment includes controlling, based on a feature value of the at least one of jet flow 100, droplets 104, or satellite drops 106 in image 124, a timing $t_c$ of starting to supply the charges from charge supply unit 46 to final jet flow droplet 102$f$ in one period T of the vibrations of vibration element 44 so as to cause variation of a side stream 109 to fall within a reference range, side stream 109 being formed by droplets 104 deflected by sorting unit 110.

According to particle sorting apparatus 1 of the present embodiment and the particle sorting method of the present embodiment, variation of each side stream 109 can be reduced. Particles 105 can be sorted more stably with higher precision.

Second Embodiment

Particle sorting apparatus 1 of the present embodiment includes a configuration similar to that of particle sorting apparatus 1 of the first embodiment, and is different therefrom mainly in the following points.

In the present embodiment, timing $t_c$ of starting to supply charges from charge supply unit 46 to final jet flow droplet 102$f$ in one period T of vibrations of vibration element 44 and light emission timing $t_s$ of strobe light 123 in one period T of vibrations of vibration element 44 are fixed. It should be noted that as with the first embodiment, light emission timing $t_s$ of strobe light 123 is in synchronization with timing $t_c$.

Controller 150 can change amplitude $V_0$ of the drive voltage applied to vibration element 44. By changing amplitude $V_0$ of the drive voltage of vibration element 44, the state of jet flow 100, droplets 104, or satellite drops 106 at timing $t_c$ of starting to supply charges from charge supply unit 46 to final jet flow droplet 102$f$ in one period T of vibrations of vibration element 44 can be changed.

Controller 150 controls charge supply unit 46 to fix timing $t_c$ of starting to supply charges from charge supply unit 46 to final jet flow droplet 102$f$ in one period T of vibrations of vibration element 44. Controller 150 controls strobe light 123 to fix light emission timing $t_s$ of strobe light 123 in one period T of vibrations of vibration element 44. It should be noted that as with the first embodiment, controller 150 controls strobe light 123 to synchronize light emission timing $t_s$ of strobe light 123 with timing $t_c$. Accordingly, image 124 of at least one of jet flow 100, droplets 104, or satellite drops 106 at timing $t_c$ can be obtained using first imaging unit 120.

Based on the feature value of at least one of jet flow 100, droplets 104, or satellite drops 106 included in image 124 obtained by first imaging unit 120, controller 150 controls amplitude $V_0$ of the drive voltage applied to vibration element 44 so as to cause variation of side stream 109 to fall within the reference range. The state of jet flow 100, droplets 104, or satellite drops 106 at timing $t_c$ of starting to supply charges from charge supply unit 46 to final jet flow droplet 102$f$ in one period T of vibrations of vibration element 44 can be maintained to fall within the appropriate range, whereby the variation of side stream 109 can be reduced.

The particle sorting method of the present embodiment includes steps similar to those in the particle sorting method of the first embodiment, and is mainly different therefrom in the following points.

In the particle sorting method of the present embodiment, while sorting particles 105 based on the identification information of particles 105 obtained by light intensity detector 99 and controller 150, amplitude $V_0$ of the drive voltage applied to vibration element 44 is controlled based on the feature value of at least one of jet flow 100, droplets 104, or satellite drops 106 in image 124 so as to cause variation of side stream 109 to fall within the reference range. The state of jet flow 100, droplets 104, or satellite drops 106 at timing $t_c$ of starting to supply charges from charge supply unit 46 to final jet flow droplet 102$f$ in one period T of vibrations of vibration element 44 can be maintained to fall within the appropriate range, whereby the variation of side stream 109 can be reduced.

Specifically, steps S1 to S4$b$ shown in FIG. 14 are performed. During steps S1 to S4$b$, controller 150 controls charge supply unit 46 to fix timing $t_c$ of starting to supply charges from charge supply unit 46 to final jet flow droplet 102$f$ in one period T of vibrations of vibration element 44, and controls strobe light 123 to fix light emission timing $t_s$ of strobe light 123 in one period T of vibrations of vibration element 44.

Steps S1 to S3 of the present embodiment are the same as steps S1 to S3 shown in FIG. 9. In the present embodiment, when the feature value does not fall within the reference feature value range, controller 150 controls amplitude $V_0$ of the drive voltage applied to vibration element 44 to cause the feature value to fall within the reference feature value range (S4b). In this way, amplitude $V_0$ of the drive voltage applied to vibration element 44 is controlled to cause the variation of side stream 109 to fall within the reference range. When amplitude $V_0$ of the drive voltage of vibration element 44 is controlled to cause the feature value to fall within the reference feature value range, the process returns to step S1.

The following describes a method for obtaining the reference feature value range of at least one of jet flow 100, droplets 104, or satellite drops 106, which is one example of the reference range of the variation of side stream 109 in the present embodiment. The method for obtaining the reference feature value range in the present embodiment is similar to the method for obtaining the reference feature value range in the first embodiment, and is mainly different therefrom in the following points.

In the present embodiment, while changing amplitude $V_0$ of the drive voltage applied to vibration element 44, image 124 of at least one of jet flow 100, droplets 104, or satellite drops 106 at timing $t_c$ of starting to supply charges from charge supply unit 46 to final jet flow droplet 102f in one period T of vibrations of vibration element 44 is obtained using first imaging unit 120. When amplitude $V_0$ of the drive voltage applied to vibration element 44 is changed, image 124 obtained by first imaging unit 120 is changed as shown in FIG. 10A to FIG. 10G, for example.

Further, while changing amplitude $V_0$ of the drive voltage applied to vibration element 44, each side stream 109 is irradiated with second illumination light 149. When side stream 109 is irradiated with second illumination light 149, a scattered light is generated in side stream 109. An image of the scattered light from side stream 109 is obtained using second imaging unit 145. When amplitude $V_0$ of the drive voltage applied to vibration element 44 is changed, the image obtained by second imaging unit 145 is changed as shown in FIG. 11 to FIG. 13, for example. As with the first embodiment, controller 150 stores image 124 shown in each of FIG. 10E and FIG. 10F as a reference image into storage unit 155.

As with the first embodiment, controller 150 performs image processing of each of the reference images stored in storage unit 155 so as to calculate a reference feature value of at least one of jet flow 100, droplets 104, or satellite drops 106. Controller 150 calculates a reference feature value range based on the reference feature value obtained from each of the reference images. Controller 150 stores the reference feature value range into storage unit 155.

The following describes effects of particle sorting apparatus 1 and the particle sorting method according to the present embodiment.

A particle sorting apparatus 1 according to the present embodiment includes a flow cell 60, a vibration element 44, a charge supply unit 46, an imaging unit (first imaging unit 120), a sorting unit 110, and a controller 150. Vibration element 44 applies vibrations to a jet flow 100 ejected from flow cell 60. Charge supply unit 46 supplies charges to a final jet flow droplet 102f, final jet flow droplet 102f being closest to a break-off point 101 of jet flow droplets 102 included in jet flow 100. The imaging unit (first imaging unit 120) obtains an image 124 of at least one of jet flow 100, droplets 104, or satellite drops 106, droplets 104 and satellite drops 106 being broken off from jet flow 100. Sorting unit 110 deflects droplets 104. Controller 150 controls, based on a feature value of the at least one of jet flow 100, droplets 104, or satellite drops 106 in image 124, an amplitude $V_0$ of a drive voltage applied to vibration element 44 so as to cause variation of a side stream 109 to fall within a reference range, side stream 109 being formed by droplets 104 deflected by sorting unit 110.

A particle sorting method according to the present embodiment includes: applying vibrations from a vibration element 44 to a jet flow 100 ejected from a flow cell 60; supplying charges from a charge supply unit 46 to a final jet flow droplet 102f, final jet flow droplet 102f being closest to a break-off point 101 of jet flow droplets 102 included in jet flow 100; obtaining, using an imaging unit (first imaging unit 120), an image 124 of at least one of jet flow 100, droplets 104, or satellite drops 106, droplets 104 and satellite drops 106 being broken off from jet flow 100; and deflecting droplets 104 using a sorting unit 110. The particle sorting method according to the present embodiment includes controlling, based on a feature value of the at least one of jet flow 100, droplets 104, or satellite drops 106 in image 124, an amplitude $V_0$ of a drive voltage applied to vibration element 44 so as to cause variation of a side stream 109 to fall within a reference range, side stream 109 being formed by droplets 104 deflected by sorting unit 110.

According to particle sorting apparatus 1 of the present embodiment and the particle sorting method of the present embodiment, variation of each side stream 109 can be reduced. Particles 105 can be sorted more stably with higher precision.

Third Embodiment

With reference to FIG. 1 to FIG. 4 and FIG. 15 to FIG. 17, the following describes a particle sorting apparatus 1 and a particle sorting method according to a third embodiment. Particle sorting apparatus 1 of the present embodiment includes a configuration similar to that of particle sorting apparatus 1 of each of the first embodiment and the second embodiment, the particle sorting method of the present embodiment includes steps similar to those of the particle sorting method of each of the first embodiment and the second embodiment, and they are mainly different therefrom in the following points.

When the size of each particle 105 becomes large, the state of jet flow 100 including particle 105, droplet 104 including particle 105, or satellite drop 106 is changed. Accordingly, when the size of particle 105 becomes large, the variation of each side stream 109 may be unable to be sufficiently reduced even when the particle sorting method of each of the first embodiment and the second embodiment is used. A degree of the change of the state of jet flow 100, droplet 104, or satellite drop 106 due to the size of particle 105 is correlated with the position of particle 105 in droplet 104 in the falling direction (z direction) of droplet 104.

In the present embodiment, in accordance with the size of particle 105 in droplet 104 and the position of particle 105 in droplet 104 in the falling direction (z direction) of droplet 104, controller 150 further controls timing $t_c$ of starting to supply charges from charge supply unit 46 to final jet flow droplet 102f in one period T of vibrations of vibration element 44. In the particle sorting method of the present embodiment, timing $t_c$ of starting to supply charges from charge supply unit 46 to final jet flow droplet 102f in one period T of vibrations of vibration element 44 is further controlled in accordance with the size of particle 105 in droplet 104 and the position of particle 105 in droplet 104 in the falling direction (z direction) of droplet 104. Accordingly, even when the size of particle 105 becomes large, the variation of each side stream 109 can be reduced.

It should be noted that the further control of timing $t_c$ is performed while sorting particles 105. Specifically, when the feature value falls within the reference feature value range in step S3 shown in FIG. 9 and FIG. 14, the further control of timing $t_c$ is performed after step S3 and before returning to step S1. When the feature value does not fall within the reference feature value range in step S3 shown in each of FIG. 9 and FIG. 14, the further control of timing $t_c$ is performed after S4 shown in FIG. 9 and before returning to step S1, or after S4b shown in FIG. 14 and before returning to step S1.

Specifically, as shown in FIG. 15 to FIG. 17, it is determined whether or not the size of particle 105 in droplet 104 is more than or equal to a reference size (S11). For example, the intensity of forward-scattered light 77f or the intensity of side-scattered light 77s is detected using light intensity detector 99 (second light detector 97 or third light detector 98) (S12). Controller 150 determines whether or not the intensity of forward-scattered light 77f or the intensity of side-scattered light 77s is more than or equal to a threshold value $I_{th}$ (S13). Threshold value $I_{th}$ is stored in storage unit 155. When the size of particle 105 is less than the reference size, i.e., when the intensity of forward-scattered light 77f or the intensity of side-scattered light 77s is less than threshold value $I_{th}$, the variation of each side stream 109 is sufficiently reduced. Hence, timing $t_c$ is the same as timing $t_c$ in the first embodiment or the second embodiment. When the size of particle 105 in droplet 104 is less than the reference size, i.e., when the intensity of forward-scattered light 77f or the intensity of side-scattered light 77s is less than threshold value $I_{th}$, the process returns to step S1 of the first embodiment or the second embodiment after step S11 (for example, steps S12 and S13).

When the size of particle 105 in droplet 104 is more than or equal to the reference size, i.e., when the intensity of forward-scattered light 77f or the intensity of side-scattered light 77s is more than or equal to threshold value $I_{th}$, the variation of each side stream 109 is large. In this case, in accordance with the position of particle 105 in droplet 104 in the falling direction (z direction) of droplet 104, controller 150 further controls timing $t_c$ of starting to supply charges from charge supply unit 46 to final jet flow droplet 102f in one period T of vibrations of vibration element 44 (S14).

One droplet 104 is generated in one period T of vibrations. One period T of vibrations corresponds to the length of droplet 104 in the falling direction (z direction) of droplet 104. Hence, the position of particle 105 in droplet 104 in the falling direction (z direction) of droplet 104 is reflected in a detection timing ΔT (see FIG. 17) of particle 105 in one period T of vibrations.

Therefore, for example, in accordance with detection timing ΔT of particle 105 in one period T of vibrations, controller 150 further controls timing $t_c$ of starting to supply charges from charge supply unit 46 to final jet flow droplet 102f in one period T of vibrations of vibration element 44 (S15). In accordance with detection timing ΔT of particle 105 in one period T of vibrations, timing $t_c$ is shifted from light emission timing $t_s$ of strobe light 123. That is, in accordance with the change of the state of jet flow 100, droplet 104, or satellite drop 106 due to the size of particle 105, timing $t_c$ is shifted from timing $t_c$ in the first embodiment or the second embodiment. In this way, the variation of each side stream 109 can be reduced sufficiently. After step S14 (for example, step S15), the process returns to step S1 of the first embodiment or the second embodiment.

In addition to the effects of particle sorting apparatus 1 and the particle sorting method according to the first embodiment, particle sorting apparatus 1 and the particle sorting method according to the present embodiment exhibit the following effects.

In particle sorting apparatus 1 of the present embodiment, in accordance with the size of particle 105 in droplet 104 and the position of particle 105 in droplet 104 in the falling direction (z direction) of droplet 104, controller 150 further controls timing $t_c$ of starting to supply charges from charge supply unit 46 to final jet flow droplet 102f in one period T of vibrations of vibration element 44.

In the particle sorting method of the present embodiment, timing $t_c$ of starting to supply charges from charge supply unit 46 to final jet flow droplet 102f in one period T of vibrations of vibration element 44 is further controlled in accordance with the size of particle 105 in droplet 104 and the position of particle 105 in droplet 104 in the falling direction (z direction) of droplet 104.

According to particle sorting apparatus 1 and the particle sorting method according to the present embodiment, charge supply unit 46 can supply charges to final jet flow droplet 102f at a more appropriate timing. The variation of side stream 109 can be reduced. Particles 105 can be sorted more stably with higher precision.

Although the present disclosure has been described and illustrated in detail, it is clearly understood that the same is by way of illustration and example only and is not to be taken by way of limitation, the scope of the present disclosure being interpreted by the terms of the appended claims.

What is claimed is:

1. A particle sorting apparatus comprising:
   a flow cell;
   a vibration element that applies vibrations to a jet flow ejected from the flow cell;
   a charge supply unit that supplies charges to a final jet flow droplet, the final jet flow droplet being closest to a break-off point of jet flow droplets included in the jet flow;
   an imaging unit that obtains an image of at least one of the jet flow, droplets or satellite drops, the droplets and the satellite drops being broken off from the jet flow;
   a sorting unit that deflects the droplets; and
   a controller that controls, based on a feature value of the at least one of the jet flow, the droplets or the satellite drops, a timing of starting to supply the charges from the charge supply unit to the final jet flow droplet in one period of the vibrations or an amplitude of a drive voltage applied to the vibration element so as to cause variation of a side stream to fall within a reference range, the feature value being calculated by performing image processing of the image, and the side stream being formed by the droplets deflected by the sorting unit.

2. The particle sorting apparatus according to claim 1, wherein the feature value includes at least one of length, width, circumferential length, or area of the final jet flow droplet.

3. The particle sorting apparatus according to claim 1, wherein the feature value includes at least one of length, lower end width, circumferential length, or area of a final constriction portion of the jet flow, the final constriction portion being connected to the final jet flow droplet.

4. The particle sorting apparatus according to claim 1, wherein the feature value includes at least one of length, circumferential length, or area of the final jet flow droplet and a final constriction portion of the jet flow, the final constriction portion being connected to the final jet flow droplet.

5. The particle sorting apparatus according to claim 1, wherein the feature value includes at least one of length, width, circumferential length, or area of the jet flow in the image, or a position of a center of gravity of the jet flow in a flow direction of the jet flow in the image.

6. The particle sorting apparatus according to claim 1, wherein the feature value includes at least one of length, width, circumferential length, or area of a first droplet, a position of a center of gravity of the first droplet in a flow direction of the jet flow, or a distance between a lower end of the final jet flow droplet and an upper end of the first droplet, the first droplet being closest to the final jet flow droplet.

7. The particle sorting apparatus according to claim 1, wherein the feature value includes at least one of length, width, circumferential length, or area of a first satellite drop of the satellite drops, a distance between a lower end of the final jet flow droplet and a lower end of the first satellite drop, or a distance between the lower end of the final jet flow droplet and an upper end of the first satellite drop, the first satellite drop being closest to the break-off point.

8. The particle sorting apparatus according to claim 1, wherein the feature value includes at least one of area or circumferential length of a final constriction portion, the final jet flow droplet, and a first satellite drop of the satellite drops between an upper end of the final constriction portion and an upper end of a first droplet, or a distance between the upper end of the final constriction portion and the upper end of the first droplet, the final constriction portion being connected to the final jet flow droplet, the first droplet being closest to the final jet flow droplet, the first satellite drop being closest to the break-off point.

9. The particle sorting apparatus according to claim 1, wherein the controller further controls the timing in accordance with a size of each of respective particles in the droplets and a position of each of the respective particles in the droplets in a falling direction of the droplets.

10. A particle sorting method comprising:
applying vibrations from a vibration element to a jet flow ejected from a flow cell;
supplying charges from a charge supply unit to a final jet flow droplet, the final jet flow droplet being closest to a break-off point of jet flow droplets included in the jet flow;
obtaining, using an imaging unit, an image of at least one of the jet flow, droplets or satellite drops, the droplets and the satellite drops being broken off from the jet flow;
deflecting the droplets using a sorting unit;
performing image processing the image to calculate a feature value of the at least one of the jet flow, droplets or the satellite drops; and
controlling, based on the feature value of the at least one of the jet flow, the droplets or the satellite drops, a timing of starting to supply the charges from the charge supply unit to the final jet flow droplet in one period of the vibrations or an amplitude of a drive voltage applied to the vibration element so as to cause variation of a side stream to fall within a reference range, the side stream being formed by the droplets deflected by the sorting unit.

11. The particle sorting method according to claim 10, further comprising controlling the timing in accordance with a size of each of particles in the droplets and a position of each of the particles in the droplets in a falling direction of each of the droplets.

* * * * *